(12) United States Patent
Tamura et al.

(10) Patent No.: US 7,550,646 B2
(45) Date of Patent: Jun. 23, 2009

(54) ABSORBENT ARTICLE WITH RESILIENT PORTION AND METHOD FOR MANUFACTURING THE SAME

(75) Inventors: Tatsuya Tamura, Kagawa (JP); Satoshi Mizutani, Kagawa (JP); Shimpei Komatsu, Kagawa (JP); Makoto Suekane, Kagawa (JP)

(73) Assignee: Uni-Charm Corporation, Ehime-ken (JP)

( * ) Notice: Subject to any disclaimer, the term of this patent is extended or adjusted under 35 U.S.C. 154(b) by 240 days.

(21) Appl. No.: 11/059,132

(22) Filed: Feb. 15, 2005

(65) Prior Publication Data

US 2005/0148973 A1   Jul. 7, 2005

Related U.S. Application Data

(63) Continuation of application No. PCT/JP03/11408, filed on Sep. 8, 2003.

(30) Foreign Application Priority Data

Sep. 9, 2002   (JP)   ............................. 2002-263453
Sep. 20, 2002  (JP)   ............................. 2002-276393

(51) Int. Cl.
    *A61F 13/533*   (2006.01)
(52) U.S. Cl. ................................. 604/380; 604/385.31
(58) Field of Classification Search ................. 604/379, 604/378, 380, 381, 385.31
    See application file for complete search history.

(56) References Cited

U.S. PATENT DOCUMENTS

| | | | | |
|---|---|---|---|---|
| 3,442,268 A | * | 5/1969 | Bird ........................... | 604/380 |
| 4,059,114 A | * | 11/1977 | Richards ..................... | 604/359 |
| 4,397,645 A | * | 8/1983 | Buell .......................... | 604/380 |
| 4,443,512 A | * | 4/1984 | Delvaux ...................... | 428/162 |
| 4,622,089 A | * | 11/1986 | Lauritzen .................... | 156/250 |
| 4,758,240 A | * | 7/1988 | Glassman .................... | 604/379 |
| 4,886,697 A | * | 12/1989 | Perdelwitz et al. .......... | 428/192 |
| 4,936,839 A | * | 6/1990 | Molee et al. ................ | 604/378 |
| 5,171,302 A | * | 12/1992 | Buell ..................... | 604/385.23 |
| 5,423,786 A | * | 6/1995 | Fung et al. .................. | 604/367 |
| 5,447,506 A | * | 9/1995 | Lindquist .................... | 604/374 |
| 5,514,104 A | * | 5/1996 | Cole et al. .................. | 604/366 |

(Continued)

FOREIGN PATENT DOCUMENTS

JP   52-138398   11/1977

(Continued)

*Primary Examiner*—Patricia M Bianco
*Assistant Examiner*—Paula L Craig
(74) *Attorney, Agent, or Firm*—Darby & Darby P.C.

(57) ABSTRACT

Disclosed is an absorbent article including: a liquid-permeable topsheet on its skin surface; a backsheet on its garment surface; and an absorbent layer therebetween. First compressed portions and second compressed portions, in which the absorbent layer is compressed together with at least the topsheet, extend longitudinally of the absorbent article. The first compressed portions are disposed symmetrically about a longitudinal centerline of the absorbent article to define a central absorbent portion having the absorbent layer therebetween. The second compressed portions are disposed symmetrically about the longitudinal centerline and spaced outwardly apart from the first compressed portions. When the central absorbent portion is laterally compressed by an external force, resilient portions each defined between each adjacent pair of first and second compressed portions are permitted to exert a resilience against compression on the central absorbent portion.

20 Claims, 14 Drawing Sheets

U.S. PATENT DOCUMENTS

| | | | | |
|---|---|---|---|---|
| 5,591,150 | A * | 1/1997 | Olsen et al. | 604/385.23 |
| 5,674,341 | A * | 10/1997 | Ng | 156/234 |
| 5,722,967 | A * | 3/1998 | Coles | 604/385.04 |
| 5,795,344 | A * | 8/1998 | Chappell | 604/379 |
| 5,981,824 | A * | 11/1999 | Luceri | 604/365 |
| 6,159,190 | A * | 12/2000 | Tanaka et al. | 604/385.24 |
| 6,312,416 | B1 * | 11/2001 | Brisebois et al. | 604/385.01 |
| 6,319,239 | B1 * | 11/2001 | Daniels et al. | 604/385.01 |
| 6,326,525 | B1 * | 12/2001 | Hamajima et al. | 604/378 |
| 6,371,948 | B1 * | 4/2002 | Mizutani | 604/385.01 |
| 6,506,961 | B1 * | 1/2003 | Levy | 604/380 |
| 6,563,013 | B1 * | 5/2003 | Murota | 604/380 |
| 6,617,490 | B1 * | 9/2003 | Chen et al. | 604/380 |
| 6,695,827 | B2 * | 2/2004 | Chen et al. | 604/385.01 |
| 6,730,068 | B2 * | 5/2004 | Kashiwagi et al. | 604/385.04 |
| 7,067,711 | B2 * | 6/2006 | Kuroda et al. | 604/380 |
| 7,078,583 | B2 * | 7/2006 | Kudo et al. | 604/380 |
| 7,122,713 | B2 * | 10/2006 | Komatsu et al. | 604/380 |
| 7,196,241 | B2 * | 3/2007 | Kinoshita et al. | 604/380 |
| 7,312,372 | B2 * | 12/2007 | Miyama et al. | 604/380 |
| 2001/0007065 | A1 * | 7/2001 | Blanchard et al. | 604/369 |
| 2001/0020157 | A1 * | 9/2001 | Mizutani et al. | 604/385.04 |
| 2001/0039406 | A1 * | 11/2001 | Hamajima et al. | 604/367 |
| 2004/0243082 | A1 * | 12/2004 | Kinoshita et al. | 604/380 |
| 2004/0249355 | A1 * | 12/2004 | Tanio et al. | 604/385.01 |
| 2004/0260262 | A1 * | 12/2004 | Nishitani et al. | 604/385.04 |
| 2005/0124951 | A1 * | 6/2005 | Kudo et al. | 604/380 |
| 2005/0148971 | A1 * | 7/2005 | Kuroda et al. | 604/380 |
| 2005/0148972 | A1 * | 7/2005 | Miyama et al. | 604/380 |
| 2007/0073253 | A1 * | 3/2007 | Miyama et al. | 604/380 |

FOREIGN PATENT DOCUMENTS

| | | |
|---|---|---|
| JP | 5-39691 | 10/1993 |
| JP | 08-322875 | 12/1996 |
| JP | 10-272156 | 10/1998 |
| JP | 10-328232 | 12/1998 |
| JP | 11-033054 | 2/1999 |
| JP | 2000-225146 | 8/2000 |
| JP | 2001-008971 | 1/2001 |
| JP | 2002-095697 | 4/2002 |
| JP | 2002-119539 | 4/2002 |
| WO | WO-00/32145 A1 | 6/2000 |

* cited by examiner

ABSORBENT ARTICLE WITH RESILIENT PORTION AND METHOD FOR MANUFACTURING THE SAME

This application is a continuation of PCT/JP03/011408 filed Sep. 8, 2003, which claims priority to Japanese Application Nos. 2002-263453 filed Sep. 9, 2002, and 2002-276393 filed Sep. 20, 2002.

BACKGROUND OF THE INVENTION

1. Field of the Invention

The present invention relates to an absorbent article suitable for absorbing menstrual blood and so on discharged from the female genital organ, more particularly, relates to an absorbent article having resilient portions for restoring the article to its original state even when it is deformed by compression or twisted during wear, and a method for manufacturing the same.

2. Related Art

Absorbent articles intended to absorb menstrual blood discharged from a female genital organ are typically constructed to include an absorbent layer, a liquid-permeable topsheet covering the skin surface of the absorbent layer, and a liquid-impermeable backsheet covering the garment surface of the absorbent layer. Generally, they are worn with the backsheet adhered to an inner side of a groin piece of an undergarment through a pressure-sensitive adhesive layer.

In order to certainly collect liquid discharged from an excretory part of a wearer by the absorbent article, the skin surface is preferably brought into close contact with the wearer's excretory part. If a clearance is caused between the skin surface of the absorbent article and the excretory part when the absorbent article is worn in the crotch, discharged liquid applied to the topsheet may flow along the topsheet to easily cause leakage laterally of the absorbent article or leakage toward the wearer's buttocks, which results in fouling the undergarment or other garments.

As disclosed in the following Patent Publications 1 to 3, therefore, there have been developed absorbent articles in which a portion between grooves formed in the skin surface is raised for close contact with the wearer's excretory part.

Patent Publication 1 discloses an absorbent article, in which a raised portion where an absorbent body is of an increased thickness is provided centrally while a pair of curved top-side grooves is formed on right and left sides of the raised portion. The top-side grooves can serve as a flexible hinge to facilitate folding of the absorbent body, which aims at deforming the raised portion to have an arc cross-section projecting toward the wearer.

Patent Publication 2 discloses an absorbent article, in which a skin contact surface has a longitudinally elongated projection surrounded by a recess. This aims at raising the projection for closely contacting the wearer's excretory part as well as at blocking liquid by the recess surrounding the projection for preventing diffusion to surroundings.

Patent Publication 3 discloses a substantially longitudinally elongated absorbent article, in which arc-shaped folding portions inwardly curved from longitudinal side edges are provided on a region where an absorbent body is present, so that leakage preventing wall forming regions are formed in the portions confined in the folding portions. The leakage preventing wall forming regions intended to rise toward the wearer's crotch at the time of wearing aim at preventing lateral leakage of discharged liquid.

[Patent Publication 1]
Japanese Unexamined Patent Publication No. 10-328232

[Patent Publication 2]
Japanese Unexamined Patent Publication No. 11-33054

[Patent Publication 3]
Japanese Unexamined Patent Publication No. 8-322875

FIG. 15 is a sectional view schematically showing a state where such an absorbent article as disclosed in Patent Publications 1 to 3 is worn.

Referring to FIG. 15, the wearer's crotch and thighs are indicated by 50 and 51, a groin piece of an undergarment to be applied to the crotch 50 is indicated by 25, and the conventional absorbent article is indicated by 60. This absorbent article 60 is adhered to and fixed on an inner side of the groin piece 25. In the foregoing Patent Publications, a pair of grooves 61, 61 is formed in the skin surface of the absorbent article 60 so that a central portion 62 between the grooves 61, 61 can closely contact an excretory part in the crotch 50.

When the absorbent article 60 is worn as attached to the groin piece 25, as shown in FIG. 15, a lateral compressive force F is frequently applied to the groin piece 25 and the absorbent article 60 from the thighs 51, 51 during walking. The compressive force makes the right and left grooves 61, 61 approach each other, so that the lateral compressive force acts on the central portion 62 between the grooves 61, 61.

In the conventional absorbent article 60, however, resiliency against the lateral compressive force mainly depends on resiliency of absorbent layer provided in the central portion 62. Because the absorbent layer in the central portion 62 need feel soft to the crotch 50 and its liquid absorption capacity need be increased, its basis weight is high, whereas its density is low. Accordingly, when compressed and deformed, as shown in FIG. 15, its lateral resiliency is so poor that its width cannot be easily restored from the compressed and deformed state. When the absorbent article is twisted as a whole in accordance with the motion of the crotch, on the other hand, it cannot be easily restored from the twisted state.

Particularly when the absorbent layer is of a high basis weight and a low density, as set forth above, its resiliency decreases after absorption of discharged liquid such as menstrual blood, so that its bulkiness cannot be restored once the central portion 62 is crushed by pressure from the crotch 50 and its lateral resiliency against compression due to the compressive force F decreases drastically. Therefore, even after the thighs 51, 51 are spread wide, the absorbent article remains compressed laterally or twisted, decreasing the area of the skin surface of the absorbent article 60 and easily forming a space between the article and the crotch 50, which easily results in causing lateral leakage.

Furthermore, since the conventional ones disclosed in the foregoing Patent Publications are all constructed such that the grooves 61 are disposed one on each side, side portions 63, 63 outside the grooves 61 easily contact the central portion 62 when deformed as shown in FIG. 15. As a result, discharged liquid applied to the central portion 62 tends to migrate to the side portions 63, 63 and diffuse laterally of the absorbent article 60. That is, the effect of diffusing discharged liquid through the grooves 61, 61 cannot be achieved, which easily results in causing lateral leakage of discharged liquid.

In order to prevent lateral leakage of discharged liquid applied to the absorbent article, there have been developed leakage preventing walls extending longitudinally and opposed laterally on the skin surface of the absorbent article. The leakage preventing walls are constructed with elastic members for producing a longitudinal elastic shrinkage force disposed on a liquid-impermeable sheet, so that the sheets rise from the skin surface due to the elastic shrinkage force.

However, the conventional absorbent article is easily deformed or twisted during wear because its shape retention may be deteriorated when the absorbent article is subjected to the compressive force F or absorbs discharged liquid. In this case, front and rear rising points of the leakage preventing walls easily move toward the longitudinal centerline due to deformation of the article or move longitudinally due to twisting of the absorbent article. Accordingly, since the standing position of the leakage preventing walls is unstable, the leakage preventing walls may possibly twist or fall down toward the longitudinal centerline, decreasing the liquid absorption area of the skin surface.

In case where the leakage preventing walls are disposed in such a long absorbent article as disclosed in Patent Publications 1 and 2, the leakage preventing walls become more unstable since the length of the leakage preventing walls need be increased. When a long absorbent article of this type is worn, the leakage preventing walls may move unexpectedly following the motion of the wearer's body, which results in causing twisting or falling down of the leakage preventing walls more easily.

SUMMARY OF THE INVENTION

The present invention has been worked out in view of the shortcomings in the prior art set forth above and has an object to provide an absorbent article, in which resiliency against lateral compression is improved to prevent leakage of discharged liquid, and a method for manufacturing the same.

Another object of the present invention is to provide an absorbent article, in which leakage preventing walls disposed on a skin surface thereof can be certainly kept in a standing position.

According to a first aspect of the present invention, there is provided an absorbent article comprising:

a liquid-permeable topsheet on a skin surface;

a backsheet on a garment surface; and an absorbent layer between the topsheet and the backsheet, wherein first compressed portions and second compressed portions, in which the absorbent layer is compressed together with at least the topsheet, extend longitudinally of the absorbent article, the first compressed portions being disposed symmetrically about a longitudinal centerline of the absorbent article to define a central absorbent portion having the absorbent layer therebetween, the second compressed portions being disposed symmetrically about the longitudinal centerline and spaced outwardly apart from the first compressed portions, wherein when the central absorbent portion is laterally compressed by an external force, resilient portions each defined between each adjacent pair of first and second compressed portions are permitted to exert a resilience against compression on the central absorbent portion.

In the absorbent article, since the resilient portions are provided between the first and second compressed portions, the absorbent article can be easily restored from a laterally compressed or twisted state to its original state due to resiliency of the resilient portions. Particularly when discharged liquid is absorbed by the central absorbent portion between the first compressed portions, the discharged liquid can be blocked by the first compressed portions to prevent the resilient portions from being wetted. Therefore, even after resiliency of the central absorbent portion is deteriorated by the absorption of discharged liquid, the resilient portions on both sides thereof can always produce sufficient resilience to restore the absorbent article from a laterally compressed or twisted state.

In the individual resilient portions, the absorbent layer may be compressed to have a higher density than in the central absorbent portion.

The resilient portions have a width that is preferably less than one half, more preferably less than one third, of a width of the central absorbent portion.

As the width of the resilient portions is decreased, the resilient portions between the first and second compressed portions may have a narrow higher-density layer, so that large resilience can be easily produced. As the resilient portions are narrowed, moreover, the resilient portions hardly feel uncomfortable against the wearer's skin.

In the individual resilient portions, the absorbent layer may be compressed due to formation of the first and second compressed portions.

In the individual resilient portions, alternatively, the absorbent layer of hydrophilic fibers may be compressed together with a nonwoven fabric of synthetic fibers due to formation of the first and second compressed portions.

In the latter case, preferably, the absorbent layer is compressed together with the nonwoven fabric also in the individual first compressed portions. For example, the nonwoven fabric may be a through-air bonded nonwoven fabric.

When not only the absorbent layer mainly comprised of hydrophilic fibers such as pulp but also the nonwoven fabric of synthetic fibers is disposed in the resilient portions, as set forth above, the resiliency can be improved more. Particularly because the resilient portions contain the synthetic fibers, the resiliency is hardly deteriorated even after the discharged liquid is applied to the resilient portions. When the first compressed portions contain the synthetic fibers, moreover, the synthetic fibers can be melted and solidified therein, so that the compressed state of the first compressed portions can be maintained even after wetted with the discharged liquid.

Between the topsheet and the backsheet, the individual resilient portions may have a resilient reinforcing member alone or in combination with the absorbent layer that is compressed due to formation of the first and second compressed portions.

The reinforcing member may be foamed urethane resin, foamed urethane resin treated to be hydrophilic, or synthetic rubber.

Preferably, the resilient portions approach each other the nearest at a lateral reference line of the absorbent article, and extend gradually away from the centerline as they extend away from the lateral reference line toward longitudinally opposed ends of the absorbent article. For example, the individual resilient portions may be in the shape of a line curved toward the centerline.

Preferably, the individual resilient portions have a portion of constant width, over which the first and second compressed portions are spaced a constant distance apart from each other.

With this construction, a force from the wearer's thighs can be almost uniformly exerted on every part of the resilient portions. In addition, the resilient portions hardly feel uncomfortable against the thighs.

The absorbent article may be constructed such that side portions are each defined between each second compressed portion and a corresponding longitudinally extending side edge of the absorbent article, and an elastic shrinkage force is longitudinally exerted on the side portions.

In this case, the side portions can rise toward the wearer's skin due to the elastic shrinkage force when applied to the wearer's crotch, thereby serving as leakage preventing walls for preventing lateral leakage. Here, since the first compressed portions, the second compressed portions and the resilient portions are disposed between the central absorbent portion and the side portions, the central absorbent portion hardly contact the side portions, so that migration of discharged liquid from the central absorbent portion to the side portions can be prevented to improve the leakage preventing effect of the side portions.

In one embodiment of the absorbent article, longitudinally extending sheets are disposed on the skin surface with the central absorbent portion externally exposed therebetween, the individual sheets being fixed on the skin surface at front and rear portions thereof while being raised from the skin surface at an intermediate portion thereof to form a leakage preventing wall, wherein at least one of front and rear rising points of the leakage preventing wall is in proximity to the second compressed portion.

The rising points may be in proximity to ends of the second compressed portion.

With the rising points of the leakage preventing wall thus provided in proximity to the second compressed portion or ends of the second compressed portion, i.e., the resilient portion, irregular motion of the rising points of the leakage preventing wall can be inhibited, thereby preventing twisting or falling down of the leakage preventing wall even when a pressure is applied from the thighs in a wet state where discharged liquid is absorbed.

In another embodiment of the absorbent article, first rear compressed portions are disposed to gradually approach each other as they extend continuously from the first compressed portions toward a rear edge of the absorbent article, and second rear compressed portions are each disposed between each first rear compressed portion and corresponding one of the side edges and spaced apart from the first rear compressed portions, wherein longitudinally extending sheets are disposed on the skin surface with the central absorbent portion externally exposed therebetween, the individual sheets being fixed on the skin surface at front and rear portions thereof while being raised from the skin surface at an intermediate portion thereof to form a leakage preventing wall, wherein a front rising point of the leakage preventing wall is in proximity to the first compressed portion while a rear rising point of the leakage preventing wall is in proximity to the second rear compressed portion.

The rear rising point of the leakage preventing wall may be in proximity to a front end of the second rear compressed portion.

Also in this case, since the rear rising point of the leakage preventing wall is subjected to resilience due to a rear resilient portion defined between the first rear compressed portion and the second rear compressed portion, irregular motion can be inhibited, thereby preventing twisting or falling down of the leakage preventing wall.

Here, the proximity preferably means that a distance is 45 mm or less, more preferably 25 mm or less.

The absorbent article of the present invention is suitable for use as a sanitary napkin.

Since sanitary napkins are worn in the crotch even during the daytime activity, they are easily contracted or twisted by a compressive force from the wearer's thighs. However, because the absorbent article of the present invention has the resilient portions, it can be easily restored from such contracted or twisted state.

According to a second aspect of the present invention, there is provided a method for manufacturing an absorbent article comprising: a liquid-permeable topsheet on a skin surface; a backsheet on a garment surface; and an absorbent layer between the topsheet and the backsheet, first compressed portions and second compressed portions, in which the absorbent layer is compressed together with at least the topsheet, extending longitudinally of the absorbent article, the first compressed portions being disposed symmetrically about a longitudinal centerline of the absorbent article, the second compressed portions being disposed symmetrically about the longitudinal centerline and spaced outwardly apart from the first compressed portions, the method comprising the step of pressing at least the absorbent layer from the skin surface with a pressure member having first projections spaced apart from each other for forming the first compressed portions and second projections disposed outside the first projections for forming the second compressed portions, wherein the pressure member has: recesses each formed between each adjacent pair of first and second projections to have a first depth from a top of the first projection; a first base formed between the first projections to have a second depth; and a second base formed outside the first projections to have a third depth, wherein the first depth is smaller than the second depth and smaller than the third depth so that the absorbent layer is more highly compressed at locations between the first and second compressed portions with the recesses than at locations confronted by the first and second bases.

In this method, it is preferred that the absorbent article is not substantially pressed with the first and second bases.

However, it is possible to lightly press the absorbent layer with the first and second bases as long as the absorbent layer has a lower density at the locations confronted by the first and second bases than at the locations pressed with the recesses.

BRIEF DESCRIPTION OF THE DRAWINGS

The present invention will be understood more fully from the detailed description given hereinafter and from the accompanying drawings of the preferred embodiments of the present invention, which, however, should not be taken to be limitative to the invention, but are for explanation and understanding only.

In the drawings:

FIGS. 14A and 14B illustrate a pressure member for forming compressed portions, wherein FIG. 14A is a fragmentary plan view and FIG. 14B is a sectional view taken along line B-B.

DESCRIPTION OF THE PREFERRED EMBODIMENT

The present invention will be discussed hereinafter in detail in terms of the preferred embodiments according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscurity of the present invention.

In the present invention, the absorbent article refers to devices which are intended to be worn in the crotch of a wearer to absorb various exudates discharged from the wearer's body, such as menstrual blood, urine, and vaginal discharge, but in the following embodiments, the absorbent article is shown embodied in a sanitary napkin whose primary object is to absorb menstrual blood discharged from the vaginal opening of a woman. It should be noted that the absorbent article has two major surfaces: of which one surface intended to be worn toward the wearer's crotch is referred to as "skin surface", while the other surface is referred to as "garment surface" regardless of whether a garment is worn outside the absorbent article or not.

As used herein, the term "compressed portions" refers to portions where an absorbent layer is highly compressed together with at least a topsheet and they remain in such a highly compressed state.

As used herein, the term "resilient portions" refers to portions which can produce a larger resilience (repulsive force) than a central absorbent portion located therebetween when the absorbent article is laterally compressed.

As used herein, the term "longitudinal centerline" refers to a line which extends longitudinally to divide the absorbent article laterally in two. On the other hand, the term "lateral reference line" does not necessarily refer to a line which extends laterally to divide the absorbent article longitudinally in two. In the following embodiments where right and left first compressed portions are not parallel with each other, a line which extends laterally at a location where the right and left first compressed portions approach each other the nearest, is taken as the lateral reference line. If the location where the right and left first compressed portions approach each other the nearest cannot be specified, such as when they are parallel with each other, a line which extends laterally to cross a longitudinal center of a portion intended to be brought into contact with the vaginal opening during wear, is taken as the lateral reference line.

Figure 1:
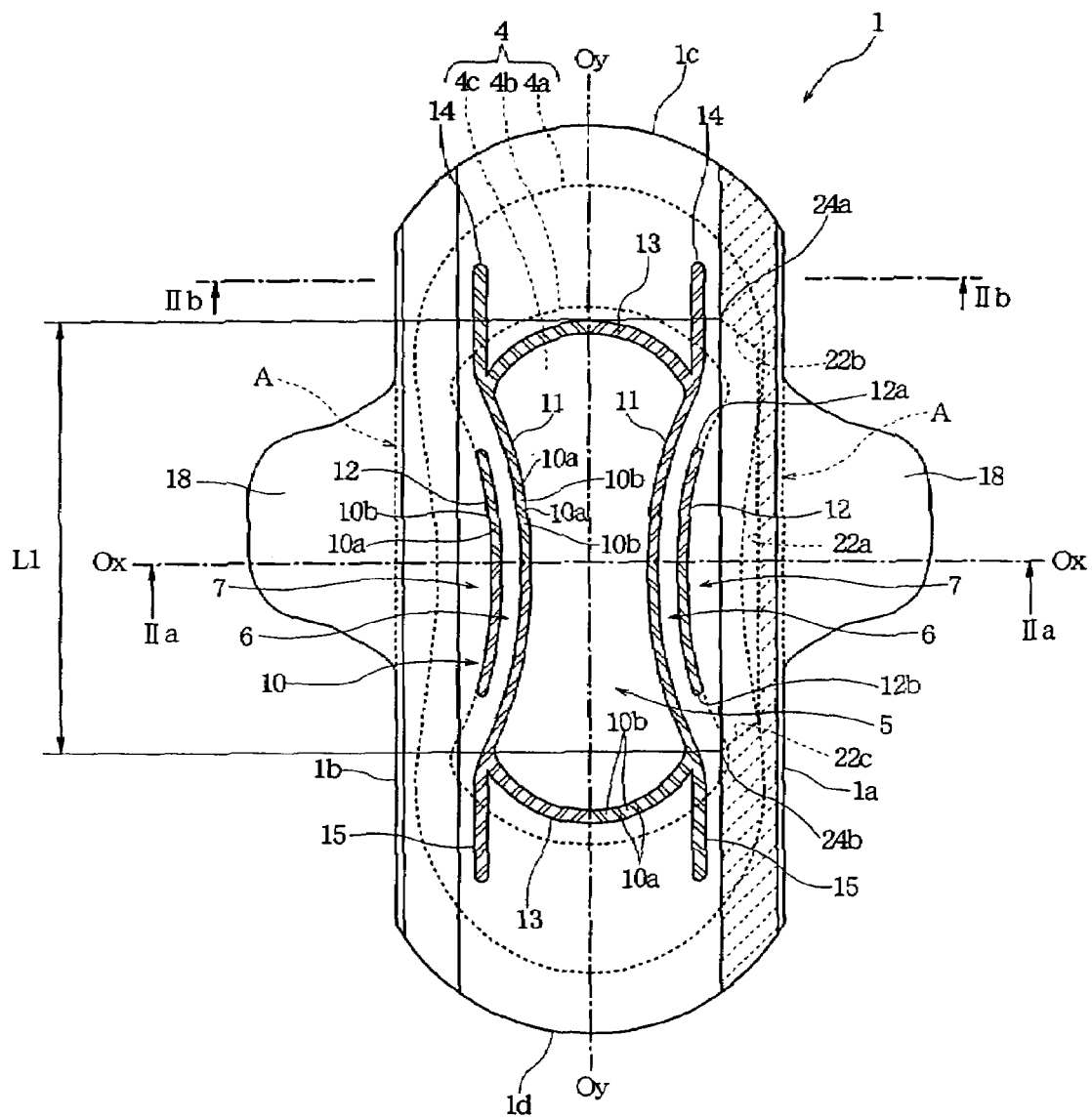
FIG. 1 is a top plan view showing a sanitary napkin as an absorbent article according to a first embodiment of the present invention.
Figure 2A:
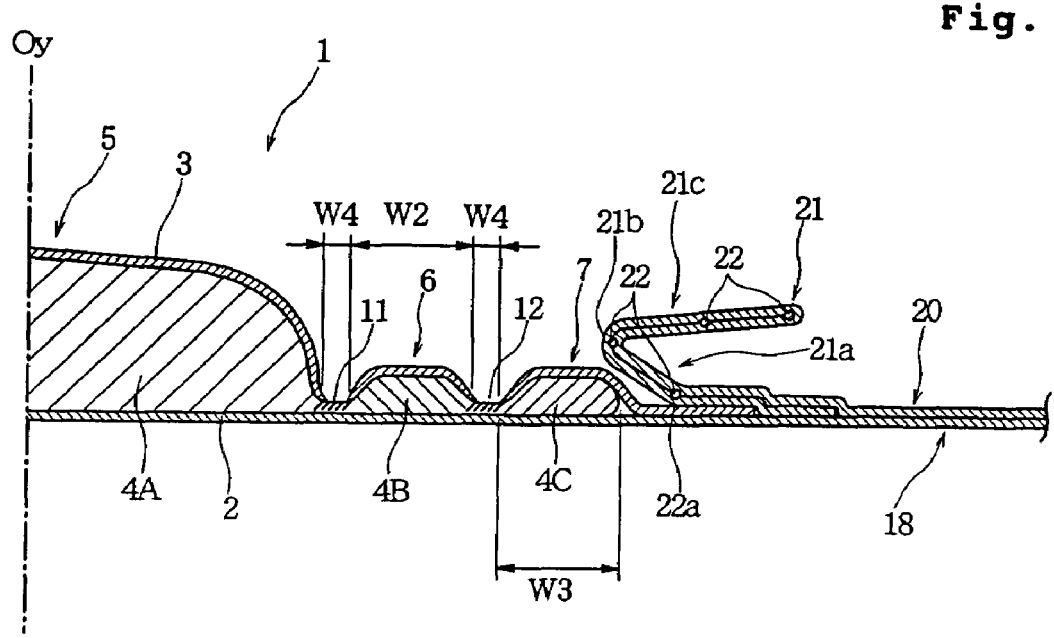
FIG. 2A is a half sectional view of the sanitary napkin taken along line IIa-IIa of FIG. 1.
Figure 2B:
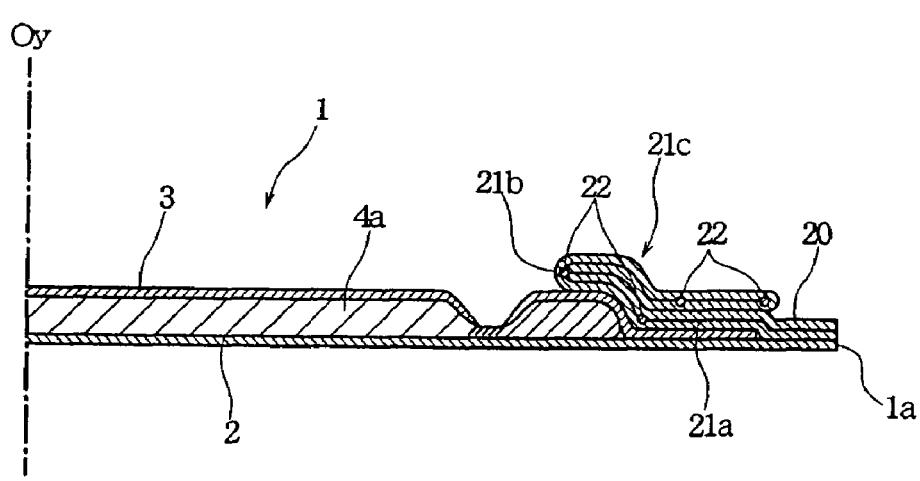
FIG. 2B is a half sectional view of the sanitary napkin taken along line IIb-IIb of FIG. 1.
Figure 3:
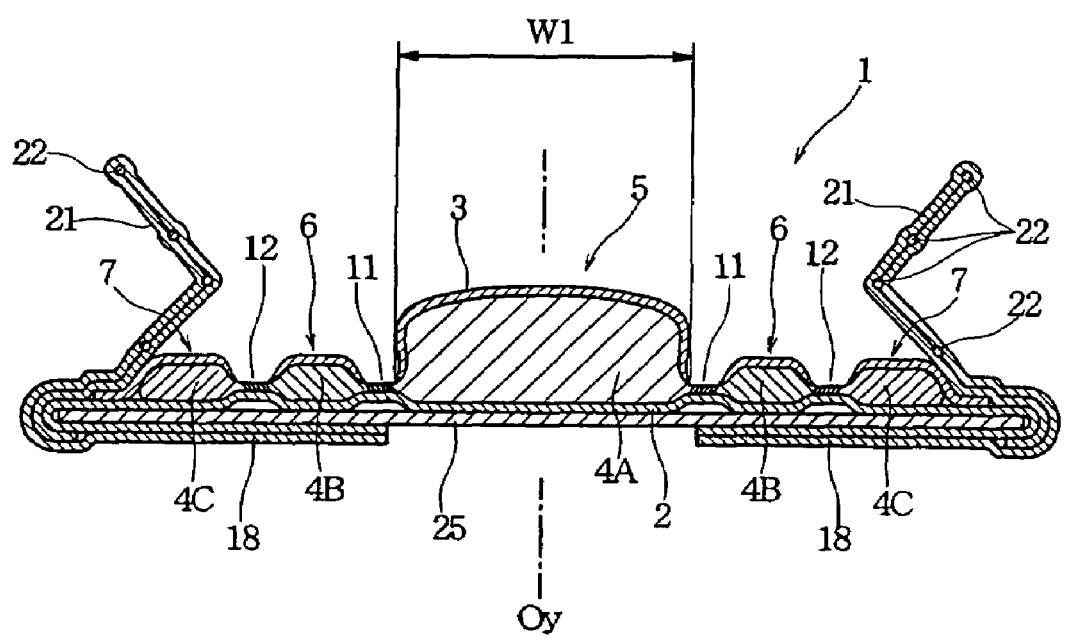
FIG. 3 is a sectional view showing a state where the sanitary napkin of FIG. 1 is attached to a groin piece of an undergarment.
Figure 4:
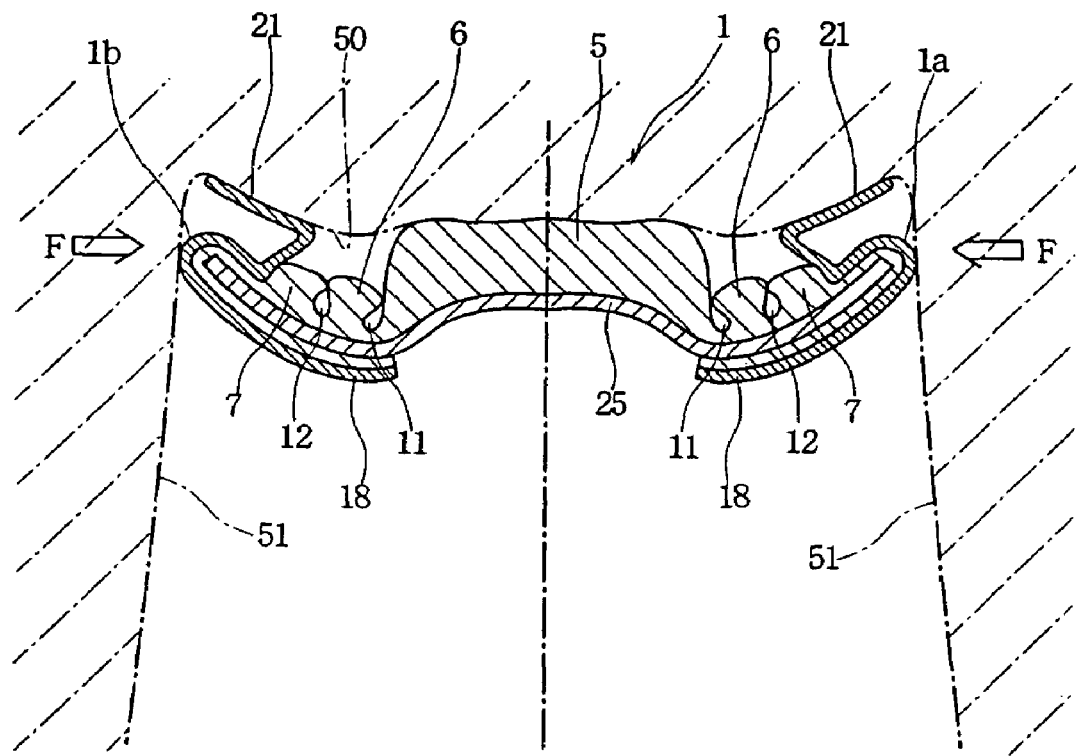
FIG. 4 is a sectional view schematically showing a state where the groin piece and the sanitary napkin are deformed due to a lateral compressive force.
Figure 5:
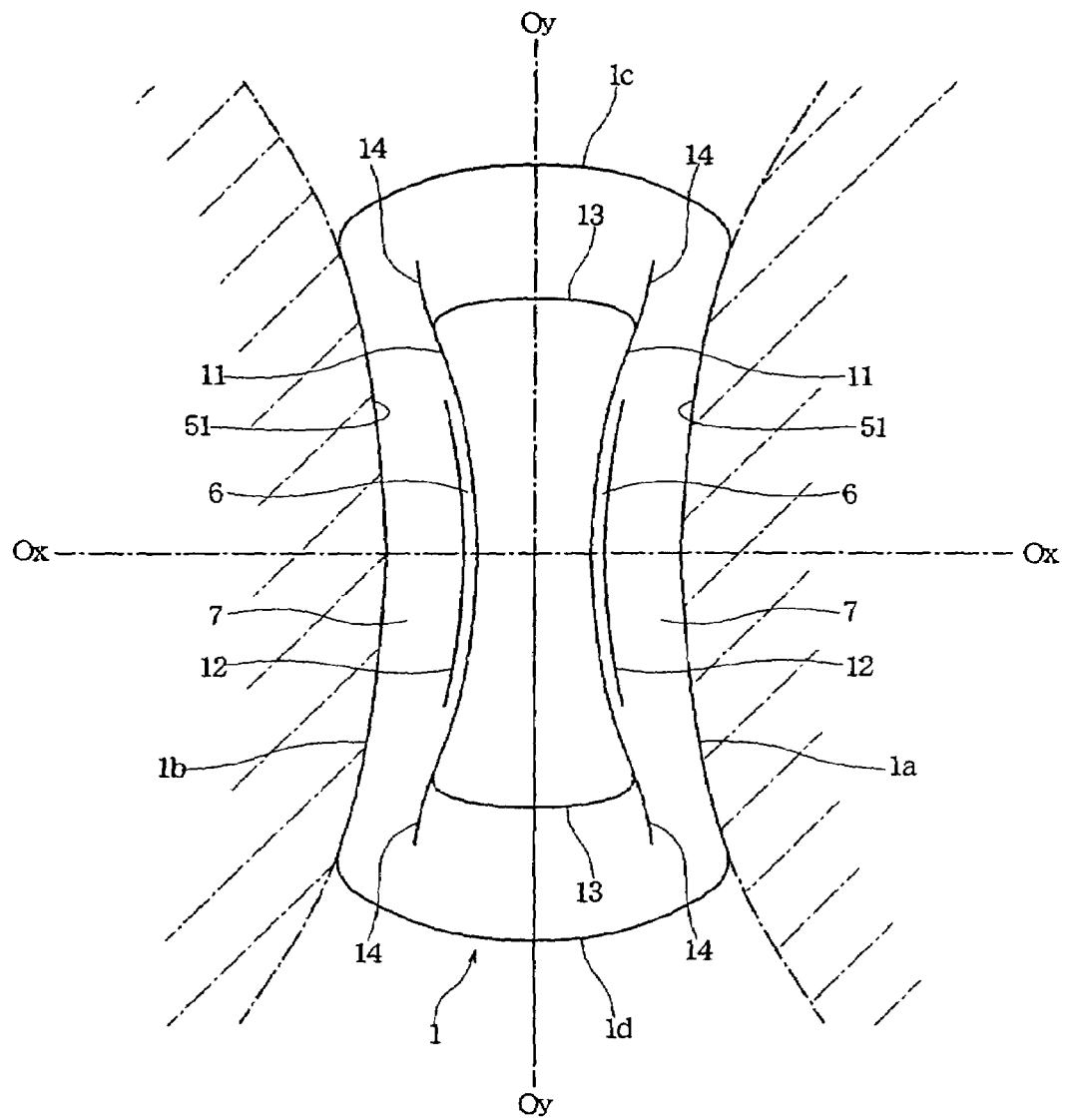
FIG. 5 is a top plan view schematically showing a state where the groin piece and the sanitary napkin are deformed due to a lateral compressive force.

FIG. 1 is a top plan view showing a sanitary napkin 1 as an absorbent article according to a first embodiment of the present invention, wherein the skin surface faces upward; FIG. 2A is a half sectional view of the sanitary napkin taken along line IIa-IIa of FIG. 1, and FIG. 2B is a half sectional view of the sanitary napkin taken along line IIb-IIb of FIG. 1; FIG. 3 is a sectional view showing a state where the sanitary napkin is attached to a groin piece of an undergarment; FIG. 4 is a sectional view schematically showing a state where the groin piece and the sanitary napkin are deformed due to a lateral compressive force; and FIG. 5 is a top plan view schematically showing the deformed state.

As shown in the top plan view of FIG. 1, the sanitary napkin 1 is of an elongated shape, wherein longitudinally extending right and left side edges 1a and 1b are laterally spaced a constant distance apart from a longitudinal centerline Oy-Oy, while front and rear end edges 1c and 1d in the shape of an outwardly curved line are longitudinally spaced apart from a lateral reference line Ox-Ox. It should be noted that in the case where the sanitary napkin is provided with wings 18 and 18, as shown in FIG. 1, the right and left side edges 1a and 1b will be described as inclusive of imaginary cut lines A and A extending along bases of the wings 18 and 18.

As shown in the sectional views of FIGS. 2 and 3, the sanitary napkin 1 has a liquid-impermeable backsheet 2 appearing on the garment surface and a liquid-permeable topsheet 3 appearing on the skin surface. Between the backsheet 2 and the topsheet 3, disposed is an absorbent layer 4. The absorbent layer 4 is constructed to include: a first absorbent layer 4a whose periphery is shown by a dotted line in FIG. 1; a second absorbent layer 4b having a smaller area than the first absorbent layer 4a and laid on the first absorbent layer 4a, whose periphery is also shown by a dotted line in FIG. 1; and a third absorbent layer 4c having a smaller area than the second absorbent layer 4b and laid on the second absorbent layer 4b within a central absorbent portion 5 of an hourglass shape.

Here, at least the topsheet 3 and the absorbent layer 4 are compressed to form compressed portions 10. The compressed portions 10 are formed by embossing with a pressure member that will be described later, wherein the first absorbent layer 4a, the second absorbent layer 4b, the third absorbent layer 4c and the topsheet 3 are stacked one upon another and then heated under pressure applied from the side of the topsheet 3. As a result, the compressed portions 10 have high-density compressed portions 10a, in which the absorbent layer and the topsheet 3 are pressed until they get almost filmy, and medium-density compressed portions 10b, in which although doesn't get filmy, the absorbent layer is of a higher density than in portions other than the compressed portion 10, between adjacent high-density compressed portions 10a. With the high-density compressed portions 10a and the medium-density compressed portions 10b alternating with each other, each compressed portion 10 forms a compressed groove where the skin surface of the sanitary napkin 1 is recessed toward the backsheet 2.

The compressed portions 10 comprise first compressed portions 11, 11 that are disposed symmetrically about the longitudinal centerline Oy-Oy and second compressed portions 12, 12 that are disposed symmetrically about the longitudinal centerline Oy-Oy and spaced outwardly apart from the first compressed portions 11, 11. The first compressed portions 11, 11 and the second compressed portions 12, 12 are compressed grooves extending along arcuate lines that are curved toward the longitudinal centerline Oy-Oy, wherein the second compressed portions 12, 12 are spaced a constant distance apart from the first compressed portion 11, 11, all along the second compressed portions 12, 12.

The compressed portions 10 also comprise lateral compressed portions 13, 13 that are connected between the first compressed portions 11, 11 at their front ends and rear ends. The lateral compressed portions 13, 13 are compressed grooves extending along arcuate lines that are curved away from the lateral reference line Ox-Ox. In this embodiment, the region surrounded by the first compressed portions 11, 11 and the lateral compressed portions 13, 13 is the central absorbent portion 5, and the second compressed portion 12, 12 are located outside the central absorbent portion.

The compressed portions 10 further comprise forwardly extending compressed portions 14, 14 that are extended continuously from the first compressed portions 11, 11 to project forwardly beyond the lateral compressed portion 13 and rearwardly extending compressed portions 15, 15 that are also extended continuously from the first compressed portions 11, 11 to project rearwardly beyond the lateral compressed portion.

The regions between the first compressed portions 11, 11 and the second compressed portions 12, 12 are resilient portions 6, 6. The resilient portions 6, 6 are arcuate regions with a constant width all along the second compressed portions 12, 12. On the other hand, the region between the right side edge 1a and the right second compressed portion 12 and the region between the left side edge 1b and the left second compressed portion 12 are side portions 7, 7.

The absorbent layer 4 is provided to extend over the central absorbent portion 5 and the resilient portions 6, 6 and further extend outwardly across the second compressed portions 12, 12 halfway through the side portions 7, 7.

In the central absorbent portion 5, the first absorbent layer 4a, the second absorbent layer 4b and the third absorbent layer 4c are stacked one upon another to provide a high-basis weight, bulky central absorbent layer 4A, as shown in FIG. 2A. On the other hand, resilient layers 4B provided in the resilient portions 6 are absorbent layers of a relatively high basis weight, in which the first absorbent layer 4a and the second absorbent layer 4b are stacked. In the resilient layer 4B, furthermore, the absorbent layer is compressed to have an increased density. In the side portions 7, then, provided are side absorbent layers 4C consisting of the first absorbent layer 4a.

The basis weight of the resilient layers 4B may be equal to or slightly less than that of the central absorbent layer 4A. However, it is preferred that the basis weight of the resilient layers 4B is greater than that of the side absorbent layers 4C so that the resilient portions 6, 6 can produce sufficient resilience.

Upon formation of the individual resilient portions 6, the topsheet 3 and the absorbent layer are pressed with embossing projections. At this time, while the topsheet 3 and the absorbent layer are heated under pressure to form the compressed grooves, the topsheet 3 subjected to the pressure from the projections is stretched laterally between the first and second compressed portions 11 and 12 that are laterally spaced only a short distance apart from each other. Between the first and second compressed portions 11 and 12, accordingly, the absorbent layer is held down due to resilience produced by the stretched topsheet 3. With the compressed portions 11 and 12 being thus formed, the resilient layer 4B in the resilient portion 6 can be made denser than the central absorbent layer 4A and the side absorbent layer 4C.

In an alternative, the high-density resilient layer 4B may be formed such that an absorbent layer that has been compressed in advance to have an increased density is fed at locations corresponding to the resilient portions 6 prior to the formation of the first and second compressed portions 11 and 12, and then the absorbent layer is compressed more with the formation of the compressed portions 11 and 12.

As shown in FIGS. 2A and 3, since the first compressed portions 11, 11 and the second compressed portions 12, 12 are compressed grooves that are recessed toward the backsheet 2, the central absorbent portion 5 and the resilient portions 6, 6 rise toward the wearer's skin. As will be described later, in the case where the resilient portions 6, 6 rise toward the wearer's skin, the central absorbent portion 5 can be easily separated from the side portions 7, 7 in a deformed state of FIG. 4.

Among the compressed portions 10, at least the first and second compressed portions 11 and 12 have a higher density (in both the high-density compressed portions 10a and the medium-density compressed portions 10b) than the central absorbent layer 4A, the side absorbent layer 4C and the resilient layer 4B. Accordingly, the first and second compressed portions 11 and 12 can serve as flexible hinges along which the sanitary napkin can be easily bent. The lateral compressed portions 13, 13, the forwardly extending compressed portions 14, 14 and the rearwardly extending compressed portions 15, 15 may also serve as flexible hinges.

As shown in FIGS. 1 and 2A, liquid-impermeable sheets 20, 20 are provided on the skin surface at two sides thereof, and the right and left liquid-impermeable sheets 20, 20 form right and left leakage preventing walls 21, 21, respectively. Because the right and left liquid-impermeable sheets 20, 20 are of symmetrical configuration and the right and left leakage preventing walls 21, 21 are of symmetrical construction about the longitudinal centerline Oy-Oy, only the right liquid-impermeable sheet 20 and the right leakage preventing wall 21 will be described hereinbelow, and the description of the left ones will be omitted, as well as the reference numerals for describing the construction of the left leakage preventing wall will be omitted from the drawings.

As shown in FIGS. 2A and 2B, the liquid-impermeable sheet 20 is folded in two with longitudinally extending elastic members 22, such as rubbers, held therebetween in a stretched state, wherein the confronting surfaces of the folded sheet are bonded together along with the elastic members 22. The liquid-impermeable sheet 20 thus folded in two has a first panel 21a and a second panel 21c resulting from further folding on a longitudinally extending fold line 21b.

The first panel 21a is bonded to the skin surface of the sanitary napkin 1 in a region hatched with dotted lines in FIG. 1. In FIG. 1, the boundary line between the bonded region and the unbonded region in the first panel 21a includes an intermediate boundary line 22a, a front boundary line 22b and a rear boundary line 22c. In the region surrounded by the boundary lines 22a, 22b and 22c (i.e., the region not hatched with dotted lines), the first panel 21a is not bonded to the skin surface.

On the other hand, the second panel 21c is laid on and bonded to the first panel 21a in a region between a front end 24a of the front boundary line 22b and the front end edge 1c, as shown in FIG. 2B. The second panel 21c is also laid on and bonded to the first panel 21a in a region between a rear end 24b of the rear boundary line 22c and the rear end edge 1d. It should be noted that the second panel 21c is not bonded to the first panel 21a in the remaining region between the front end 24a and the rear end 24b.

The elastic members 22 are provided to extend at least over the region between the front end 24a and the rear end 24b, so that in a free state where no external force is exerted on the sanitary napkin 1, an elastic shrinkage force acts on the second panel 21c of the liquid-impermeable sheet 20 in such a manner as to make the front end 24a and the rear end 24b approach each other. Between the front end 24a and the rear end 24b, accordingly, the first panel 21a and the second panel 21c rise from the intermediate boundary line 22a to thereby form the leakage preventing wall 21 of a length L1.

Here, the front end 24a of the front boundary line 22b is referred to as front rising point of the leakage preventing wall 21, while the rear end 24b of the rear boundary line 22c is referred to as rear rising point of the leakage preventing wall 21.

In the sanitary napkin 1, the front rising point 24a of the leakage preventing wall 21 is in proximity to a front end 12a of the second compressed portion 12, i.e., in proximity to a front end of the resilient portion 6. The least straight-line distance between the front rising point 24a and the front end 12a of the second compressed portion 12 is 45 mm or less, preferably 40 mm or less.

Likewise, the rear rising point 24b of the leakage preventing wall 21 is in proximity to a rear end 12b of the second compressed portion 12, i.e., in proximity to a rear end of the resilient portion 6. The least straight-line distance between the rear rising point 24b and the rear end 12b of the second compressed portion 12 is 45 mm or less, preferably 30 mm or less.

Here, the straight-line distance between the rear rising point 24b and the rear end 12b is preferably smaller than the straight-line distance between the front rising point 24a and the front end 12a. This is because when the sanitary napkin 1 is worn, the rear rising point 24b close to the wearer's buttocks tends to move more freely. The motion of the rear rising point 24b can be easily inhibited with the rear rising point 24b thus located in proximity to the resilient portion 6.

As shown in FIG. 1, the sanitary napkin 1 has the wings 18, 18 projecting outwardly from the right side edge 1a and the left side edge 1b. The wings 18, 18 are constructed with the backsheet 2 and the liquid-impermeable sheets 20 bonded together.

On an exterior surface of the backsheet 2, there are provided a pressure-sensitive adhesive layer (not shown) for bonding a central portion of the sanitary napkin 1 to a groin piece of an undergarment and a pressure-sensitive adhesive layer (not shown) for bonding the wings 18, 18 to an outer side of the groin piece of the undergarment.

FIG. 3 shows a state where the sanitary napkin 1 is attached to a groin piece 25 of an undergarment.

The sanitary napkin 1 is centrally bonded to an inner side of the groin piece 25 through the pressure-sensitive adhesive disposed on the exterior surface of the backsheet 2. On the other hand, the wings 18, 18 are folded back against the outer side of the groin piece 25 so as to be wrapped around two side edges of the groin piece 25, whereby the wings 18, 18 are bonded to the outer side of the groin piece 25 through the pressure-sensitive adhesive.

When the undergarment is worn to bring the sanitary napkin 1 into contact with the wearer's crotch, the sanitary napkin 1 tends to deform along the surface of the wearer's crotch. At this time, since the first compressed portions 11, 11 and the second compressed portions 12, 12 can serve as the flexible hinges, the sanitary napkin 1 can be easily deformed to have its skin surface recessed, as shown in the section of FIG. 4. In addition, since the sanitary napkin is recessed also in the longitudinally direction to have the front end edge 1c and the rear end edge 1d approach each other, the leakage preventing walls 21, 21 subjected to the longitudinal shrinkage force of the elastic members 22 rise from the skin surface to come into contact with the wearer's crotch, as shown in FIG. 4.

Here, since the longitudinal shrinkage force of the elastic members 22 also acts on the side portions 7, 7, the side portions 7, 7 tend to bend inwardly upwardly in FIG. 3 with the second compressed portions 12, 12 serving as the flexible hinges. Therefore, the side portions 7, 7 rise slightly slantwise with the right side edge 1a and the left side edge 1b facing toward the wearer's body, as shown in FIG. 4, so that lateral leakage of menstrual blood can be easily prevented by the slanted side portions 7, 7 and the leakage preventing walls 21, 21 rising from the side portions 7, 7.

As shown in FIG. 4, moreover, since the side portions 7, 7 rise toward the wearer's crotch 50 from the second compressed portions 12, 12, the leakage preventing walls 21, 21 are supported from below by the side portions 7, 7 containing the side absorbent layers 4C, 4C, so that the leakage preventing walls 21, 21 can be certainly kept in close contact with the wearer's crotch. At this time, since the side portions 7, 7 are located beneath the leakage preventing walls 21, 21 and halfway through the thickness of the deformed sanitary napkin 1 and the protruding resilient portions 6, 6 are located inside the side portions 7, 7, the leakage preventing walls 21, 21 may possibly contact the side portions 7, 7 but hardly contact the resilient portions 6, 6. Accordingly, even if menstrual blood flowing along the wearer's crotch is adhered to the leakage preventing walls 21, 21, the menstrual blood can be prevented from contacting the resilient portions 6, 6. As a result, since the resilient portions 6, 6 are hardly wetted, their resiliency can be prevented from deteriorating.

Furthermore, front and rear portions of the sanitary napkin 1 can be bent with the lateral compressed portions 13, 13 serving as the flexible hinges, so that the front portion forward from the lateral compressed portion 13 contacts the mons pubis while the rear potion rearward from the lateral compressed portion 13 contacts the buttocks. Still furthermore, the front portion can deform to conform to the mons pubis with the forwardly extending compressed portions 14, 14 serving as the flexible hinges, while the rear portion can deform to conform to the buttocks with the rearwardly extending compressed portions 15, 15 serving as the flexible hinges. In the front portion forward from the lateral compressed portion 13 and the rear potion rearward from the lateral compressed portion 13, moreover, since there are present the forwardly extending compressed portions 14, 14 and the rearwardly extending compressed portions 15, 15, which are arranged in longitudinal pairs, the front and rear portions can be made stiff enough to withstand twisting or distortion, so that the sanitary napkin 1 can easily be kept flat in the front and rear portions.

When the distance between thighs 51, 51 is narrowed during wear of the sanitary napkin 1, a lateral compressive force F acts on the groin piece 25 and the sanitary napkin 1 from the thighs 51, 51. The compressive force F functions to shorten the width of the sanitary napkin 1 and also acts on the resilient portions 6, 6 as a force toward the longitudinal centerline Oy-Oy.

Here, since the sanitary napkin 1 is of a constant width, the compressive force F acts particularly strongly along the lateral reference line Ox-Ox to shorten the width. However, the resilient portions 6, 6 between the first and second compressed portions 11 and 12 are in the shape of a curved line, and as shown in FIG. 5, the resilient portions 6, 6 are located along the curved surfaces of the inner sides of the thighs 51, 51 to be spaced an almost constant distance apart from the inner sides of the thighs 51, 51, all along the resilient portions 6, 6. Therefore, the compressive force F uniformly acts on the entire length of the resilient portions 6, 6 without producing a great difference in force.

Thus, since the compressive force F is uniformly exerted on every part of the stiff resilient portions 6, 6, the compressive force is not concentrated at the lateral reference line Ox-Ox but distributed longitudinally to act on the central absorbent portion 5 between the resilient portions 6, 6. Therefore, the width of the central absorbent portion 5 can be uniformly shortened without causing extreme partial narrowing.

As the high-density, stiff resilient portions 6, 6 approach each other, moreover, the central absorbent portion 5 provided therebetween is pushed up toward the wearer's body and pressed against the crotch 50. Thus, the central absorbent portion 5 comes into close contact with the vaginal opening. In this state, the resilient portions 6, 6 function to support the central absorbent portion 5 from below, thereby keeping the central absorbent portion 5 in close contact with the vaginal opening.

The resilient layers 4B, 4B of the resilient portions 6, 6, in which the absorbent layer is compressed to have an increased density, are highly laterally resilient. Therefore, when the thighs 51, 51 are spread wide, the central absorbent portion 5 can be easily laterally restored due to the resiliency of the resilient portions 6, 6. Moreover, even if the sanitary napkin 1 is twisted during wear, the twisted sanitary napkin can be easily restored due to the resiliency of the resilient portions 6, 6. Particularly because the resilient portions 6, 6 are of a constant width and curved along the thighs 51, 51, the compressive force F acting on the resilient portions 6, 6 can be relieved substantially simultaneously and uniformly for every part of the resilient portions 6, 6 when the thighs 51, 51 are spread wide, so that the width can be uniformly restored for every part of the central absorbent portion 5.

It should be noted that the first compressed portions 11, the second compressed portions 12 and the resilient portions 6 are preferably curved as shown in Figures, so as to minimize the variation in distance between respective parts of the individual resilient portions 6, 6 and the thighs 51, 51 so that the compressive force F can be applied to the resilient portions 6, 6 as uniformly as possible and the compression can be relieved as uniformly as possible when the compressive force F is released. However, a similar effect can be obtained as long as the first compressed portions 11, the second compressed portions 12 and the resilient portions 6 approach each other the nearest at the lateral centerline Ox-Ox and extend away from the longitudinal centerline Oy-Oy as they extend longitudinally away from the lateral centerline Ox-Ox. The compressed portions 11, 12 and the resilient portions 6, 6 may extend in the shape of an arc of a circle or ellipse, a trapezoid or a "V", for example. The first compressed portions 11 and the second compressed portions 12 may extend in the shape of a zigzag line or wavy line, as long as they approach each other the nearest at the lateral centerline Ox-Ox and extend away from the longitudinal centerline Oy-Oy as they extend longitudinally away from the lateral centerline Ox-Ox.

Menstrual blood discharged from the vaginal opening is mainly applied to the central absorbent portion 5 that is in close contact with the vaginal opening and is passed through the topsheet 3 and then absorbed by the central absorbent layer 4A. Since the central absorbent portion 5 is surrounded by the first compressed portions 11, 11 and the lateral compressed portions 13, 13, outward diffusion of menstrual blood can be easily prevented by these compressed portions, so that the menstrual blood can be diffused in and absorbed by the central absorbent portion 5, thereby fully exploiting the liquid absorption capacity of the central absorbent layer 4A.

When the central absorbent layer 4A of a high basis weight and a low density absorbs menstrual blood, its resiliency against compression will be deteriorated. On the other hand, since the resilient layers 4B, 4B in the resilient portions 6, 6 are highly compressed, their resiliency can be maintained even if the menstrual blood infiltrates them. Accordingly, even in a wet state where the menstrual blood is given thereto, the width of the central absorbent portion 5 can be restored every time the thighs 51, 51 are spread wide. In addition, since the central absorbent portion 5 is pressed against the vaginal opening by the resilient portions 6, 6, it is hardly spaced apart from the vaginal opening even if the menstrual blood given to the central absorbent layer 4A deteriorates compression recovery properties.

Furthermore, when the sanitary napkin 1 is laterally compressed, as shown in FIG. 4, the resilient portions 6, 6 are located at both sides of the central absorbent portion 5 and the side portions 7, 7 are located outside of them. Therefore, the surfaces of the side portions 7, 7 hardly directly contact the surface of the central absorbent portion 5. Accordingly, the menstrual blood absorbed in the central absorbent portion 5 hardly migrates to the side portions 7, 7, thereby preventing undesirable diffusion of menstrual blood. In addition, even when the menstrual blood flows laterally along the surface of the central absorbent portion 5, it can be received and blocked by the resilient portions 6, 6, thereby preventing the flow toward the side portions 7, 7.

With the resilient portions 6, 6 thus provided at right and left sides, the deformed sanitary napkin 1 can be restored to its original state immediately, especially at portions adjacent to the resilient portions 6, 6.

The deformed sanitary napkin 1 can be likewise restored even after absorption of the menstrual blood. As has been described hereinbefore, the front rising point 24a and the rear rising point 24b of the leakage preventing wall 21 are both in proximity to the resilient portion 6 with the straight-line distance being set at 45 mm or less. Therefore, even when the sanitary napkin 1 is deformed during wear to have the rising points 24a, 24b approach the longitudinal centerline Oy-Oy, they can be easily restored to their original positions after the external force is relieved. Accordingly, the leakage preventing walls 21 can be prevented from undesirably twisting, and in addition, since the positions of the rising points 24a, 24b are stabilized, the leakage preventing walls 21, 21 can be prevented from falling down to cover the surface of the central absorbent portion 5. As a result, the effect of preventing lateral leakage of menstrual blood can be improved by the leakage preventing walls 21, 21.

Here, since the first compressed portions 11, the second compressed portions 12 and the resilient portions 6 are curved toward the longitudinal centerline Oy-Oy, the front and rear ends 12a and 12b of the second compressed portion 12 easily approach the rising points 24a and 24b, so that the positions of the rising points 24a and 24b can be easily stabilized with the resilient portions 6.

In the embodiment shown in FIG. 1, the front rising point 24a is located forward of the front end 12a of the second compressed portion 12, but it should be noted that the rising point 24a may be located between the second compressed portion 12 and the right side edge 1a or the rear rising point 24b may be located between the second compressed portion 12 and the right side edge 1a. Here, the least straight-line distance between the rising point 24a or 24b and the second compressed portion 12 is preferably 45 mm or less, more preferably 25 mm or less.

Hereinbelow, preferred values for the individual components will be described. Also in other embodiments that will be described later, it is preferred that the portions having the same construction as those in the first embodiment are of similar values. Hereinbelow, although the absorbent layer is constructed by wrapping fibers such as pulp in a hydrophilic paper or the like, the density and basis weight of the absorbent layer are measured without the hydrophilic paper or the like.

Preferably, the central absorbent layer 4A is of a large liquid absorption capacity so as to be able to absorb menstrual blood sufficiently in the central absorbent portion 5. Also preferably, it is soft to the touch and so resilient as to be able to restore its thickness when a pressure exerted thereon from the wearer's body is relieved.

The central absorbent layer 4A preferably has a density in the range of 0.05 to 0.15 g/cm$^3$. The central absorbent layer 4A preferably has a basis weight from 500 to 1200 g/m$^2$, more preferably, from 500 to 1000 g/m$^2$. If they are set within the above-mentioned ranges, sufficient liquid absorption capacity and sufficient resiliency against vertical compression can be realized.

The central absorbent portion 5 has a width W1 at the lateral reference line Ox-Ox, which is preferably in the range of 15 to 50 mm, more preferably in the range of 20 to 40 mm. The first reason is that the crotch width of average women is about 30 mm. The second reason is that even if the side portions 7, 7 and the leakage preventing walls 21, 21 fall down toward the longitudinal centerline Oy-Oy, a certain area of the surface of the central absorbent portion 5 can be kept exposed for receiving menstrual blood as long as the width W1 is set within the above-mentioned range.

The resilient layers 4B provided in the resilient potions 6 have a higher density than the central absorbent layer 4A and the side absorbent layers 4C, but the thickness of the resilient portions 6 is not very small.

More specifically, the resilient portions 6 are formed such that an absorbent layer having a basis weight from 300 to 800 g/m$^2$, preferably from 350 to 600 g/m$^2$, is compressed and squeezed at locations between the first and second compressed portions 11, 12 having a width W4 from 1.5 to 3.5 mm, to thereby increase the density of the absorbent layer to 0.1 to 0.25 g/cm$^3$.

Furthermore, the resilient portions 6 are shaped to protrude with a width W2 of 3 to 10 mm and a thickness of 2 to 6 mm from the exterior surface of the backsheet 2 to the exteriors surface of the topsheet 3.

With this construction, the resilient portions 6, 6 provided between the central absorbent portion 5 and the side portions 7, 7 can be made firm and highly resilient. In addition, their bulkiness and resiliency can be prevented from decreasing even when wet.

In the central absorbent portion 5 and the resilient portions 6, 6, an additional layer such as nonwoven fabric of synthetic fibers may be provided, together with the absorbent layer of hydrophilic fibers, between the topsheet 3 and the backsheet 2, as will be described later. In this case, the preferred density range refers to the density of the absorbent layer exclusive of the nonwoven fabric, while the preferred basis weight refers to that of the absorbent layer inclusive of the nonwoven fabric.

Figure 10:
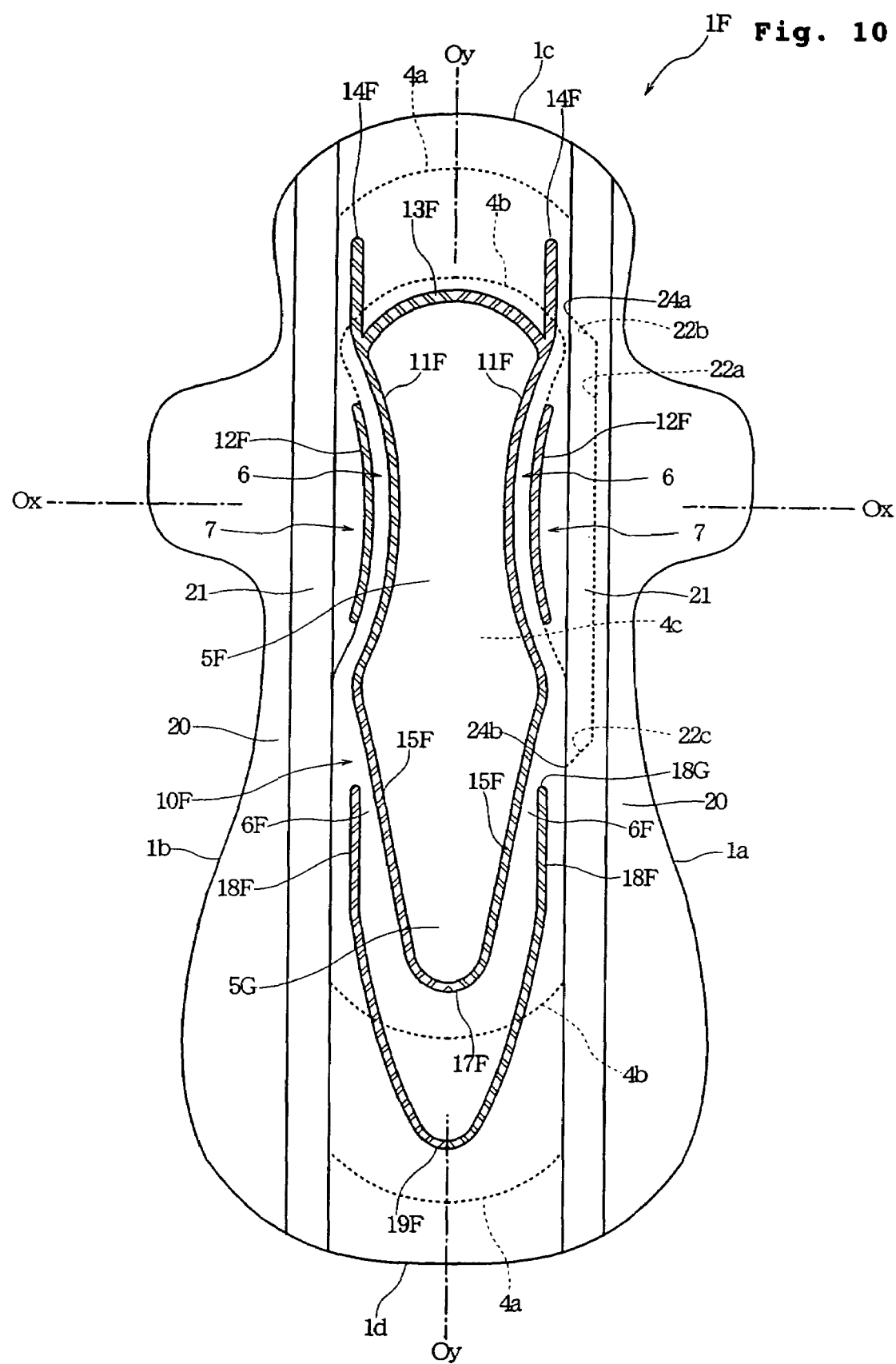
FIG. 10 is a top plan view showing a sanitary napkin according to a sixth embodiment of the present invention.

The length (dimension measured in parallel with the longitudinal centerline Oy-Oy) of the resilient portions 6, 6 depends on the length of the second compressed portions 12, 12. If the length of the resilient portions 6, 6 is too short, the width of the central absorbent portion 5 cannot be restored sufficiently; if it is too long, the stiffness of the whole sanitary napkin is excessively increased so that it feels uncomfortable against the wearer's crotch. The length of the resilient portions 6, 6 is preferably from 40 mm to 100 mm. However, in case of long-type sanitary napkins for night-time use or heavy menstrual bleeding such as shown in FIG. 10, the length of the resilient portions 6, 6 may be in excess of 100 mm. For example, when the sanitary napkin is the long type having a length of about 380 mm, the upper limit of the length of the resilient portions 6, 6 is about 120 mm. If the length is in excess of 100 mm (in excess of 120 mm in case of the long type), the sanitary napkin 1 may possibly feel stiff against the wearer's body.

The side absorbent layers 4C have a density in the range of 0.05 to 0.15 g/cm$^3$, which is lower than that of the resilient layers 4B but preferably almost similar to that of the central absorbent layer 4A. On the other hand, the side absorbent layers 4C have a basis weight which is lower than that of the resilient layers 4B, and for example, preferably about 300 to 450 g/m$^2$. The side absorbent layers 4C have a width W3, which is preferably in the range of 10 to 35 mm, more preferably in the range of 10 to 20 mm.

The upper limit of the basis weight should not be limited to the above-mentioned range, but may be 600 g/m$^2$ in case of sanitary napkins.

In the first and second compressed portions 11, 12 of the compressed portions 10, it is preferred that the density of the most densified portions, i.e., the high-density compressed portions 10a is sufficiently higher than those of the central absorbent layer 4A, the resilient layers 4B and the side absorbent layers 4C. In order that the resilient portions 6, 6 can independently produce sufficient resilience, the density of the high-density compressed portions 10a need be at least 0.3 g/cm$^3$ and is preferably in the range of 0.5 to 1.5 g/cm$^3$. Here, the density of the medium-density compressed portions 10b in the compressed portions 10 need not be set in the above-mentioned range so as to provide the resilient portions 6, 6 with sufficient resiliency. However, it is also preferred to set the density of the medium-density compressed portions 10b in the above-mentioned range so as to keep the density of the resilient portions 6, 6 high and facilitate folding on the first compressed portions 11, 11 and the second compressed portions 12, 12.

Next, preferred materials for the individual components will be described.

For the topsheet 3, a synthetic resin film formed with a large number of liquid passage holes, a synthetic resin film formed in the shape of a net or a through-air bonded nonwoven fabric of chemical fibers may be used. In an alternative, a composite material, in which the synthetic resin film having the liquid passage holes appears on the skin surface and the through-air bonded nonwoven fabric is laid beneath it, may be used. In this case, the synthetic resin film is formed of polyethylene resin containing titanium oxide as a whitening agent, while the through-air bonded nonwoven fabric is formed of sheath/core bicomponent synthetic fibers of which the core component is polyethylene terephthalate (PET) containing titanium oxide and the sheath component is polyethylene (PE), the sheath/core bicomponent synthetic fibers being thermally fusion-bonded together by means of hot air.

It is also possible to use different nonwoven fabrics such as spunlaced nonwoven fabric, spunbonded nonwoven fabric and the like for the topsheet 3.

The backsheet 2 is a liquid-impermeable, breathable sheet such as a polyethylene (PE) or polypropylene (PP) film formed with minute pores. The minute pores may be appropriately distributed over the film for improving breathability such as by adding inorganic filler such as $CaCO_3$ and $BaSO_4$ to the plastic film, followed by drawing. The film may have a thickness of about 15 to 50 μm. In an alternative, a material in which a thermoplastic resin is laminated to a nonwoven fabric may be used.

The first absorbent layer 4a, the second absorbent layer 4b and the third absorbent layer 4c are formed by accumulating fluff pulp such as ground pulp, mercerized pulp or crosslinked pulp. After stacked one upon another, the absorbent layers 4a, 4b and 4c are entirely wrapped in a hydrophilic paper. The pulp may be mixed with synthetic absorbent polymer such as polyacrylate, polyacrylamide and maleic anhydride or natural absorbent polymer such as starch and cellulose. In an alternative, absorbent polymer in the form of sheet may be contained therein.

Particularly in the case where the absorbent polymer, which may be in the form of sheet, is contained in the resilient portions 6, 6, the bonding strength between pulp can be increased when they are wetted by absorption of menstrual blood, thereby increasing the stiffness of the resilient portions 6, 6.

For the liquid-impermeable sheets 20 for forming the leakage preventing walls 21, a spunbonded nonwoven fabric, a meltblown nonwoven fabric or a laminate thereof may be used. Preferably, the sheets 20 are treated to be water-repellent.

In appropriate portions but for the compressed portions 10, the backsheet 2, the topsheet 3, the absorbent layer 4 and the liquid-impermeable sheets 20 are bonded to each other through an adhesive.

In the followings, other embodiments of the present invention will be described. Hereinafter, the detailed description of the portions having the same construction as those of the first embodiment will be omitted by designating them by the common reference numerals.

Figure 6:
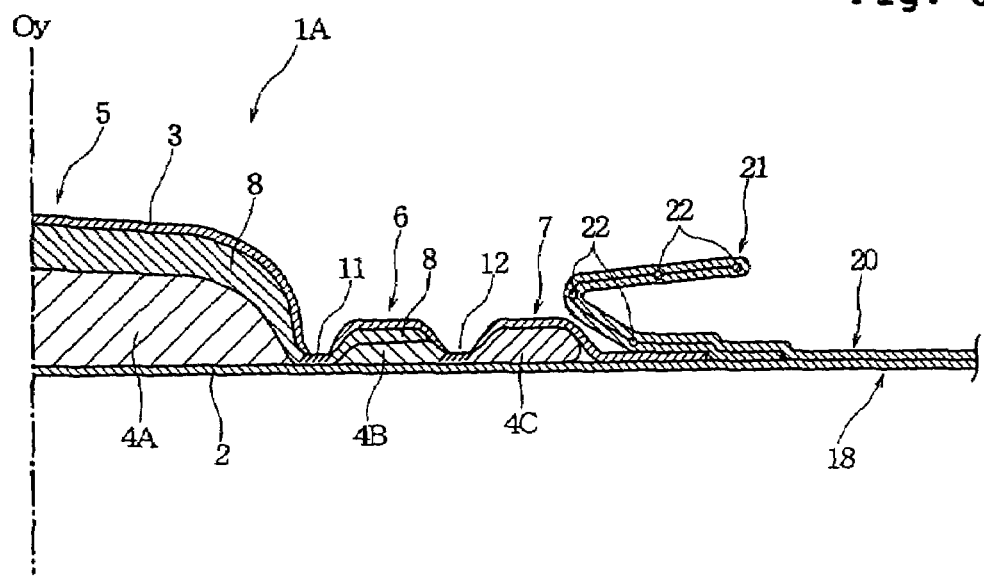
FIG. 6 is a half sectional view showing a sanitary napkin according to a second embodiment of the present invention.

FIG. 6 is a half sectional view showing a sanitary napkin 1A according to a second embodiment of the present invention.

In this embodiment, a nonwoven fabric 8 of synthetic fibers is laid on the absorbent layers 4A and 4B to extend from the central absorbent portion 5, beyond the first compressed portions 11, 11, to the resilient portions. This nonwoven fabric may be a through-air bonded nonwoven fabric, for example.

The through-air bonded nonwoven fabric may be formed such that eccentric sheath/core bicomponent synthetic fibers (e.g., having fineness of 4.4 dtex and length of 50 mm) of which the core component is polypropylene (PP) and the sheath component is polyethylene (PE) are heat treated for one minute with hot air of 135 degrees centigrade, wherein the fibers are coated with a hydrophilic lubricant. The through-air bonded nonwoven fabric has a density which is lower than those of the central absorbent layer 4A and the topsheet 3 and is in the range of 0.005 to 0.3 g/cm$^3$. The through-air bonded nonwoven fabric has a thickness of 0.5 to 2 mm and is folded in two or three for use.

In the central absorbent portion 5, since the through-air bonded nonwoven fabric is disposed between the central absorbent layer 4A, which is formed of hydrophilic fibers such as pulp or a mixture of hydrophilic fibers and absorbent polymer and wrapped in a hydrophilic paper, and the topsheet 3, menstrual blood applied to the topsheet 3 in the central absorbent portion 5 can be passed through the topsheet 3, passed through the through-air bonded nonwoven fabric due to its own weight via voids between fibers, and then absorbed by the central absorbent layer 4A. Accordingly, the absorption rate of repeatedly applied menstrual blood can be increased, and the topsheet 3 can be easily kept dry. In addition, since the through-air bonded nonwoven fabric is highly resilient, the central absorbent portion 5 itself can produce some lateral resilience when the central absorbent portion 5 is compressed laterally to decrease its width as shown in FIGS. 4 and 5.

In the resilient portions 6, 6, the through-air bonded nonwoven fabric is held between the backsheet 2 and the topsheet 3, while being compressed together with the resilient layers 4B, which is formed by wrapping a layer of pulp or a layer of pulp and absorbent polymer in a hydrophilic paper. Accordingly, the resiliency of the resilient portions 6, 6 can be improved more.

In the first compressed portions 11, the through-air bonded nonwoven fabric is heated under pressure together with the absorbent layer, so that the synthetic fibers constituting the through-air bonded nonwoven fabric are thermally fused. Therefore, the first compressed portions 11 can be maintained in the compressed state, without causing the problem of restoration of the first compressed portions 11 from the compressed and fixed state upon contact with menstrual blood. Accordingly, the density inside the resilient portions 6 can be kept high at all times.

It is more preferred that the through-air bonded nonwoven fabric is present also in the second compressed portions 12.

Here, the nonwoven fabric of synthetic fibers should not construed as limited to the through-air bonded nonwoven fabric, but different nonwoven fabrics such as spunbonded nonwoven fabric, meltblown nonwoven fabric and the like may be provided in the resilient portions 6, the first compressed portions 11 and the second compressed portions 12.

Figure 7:
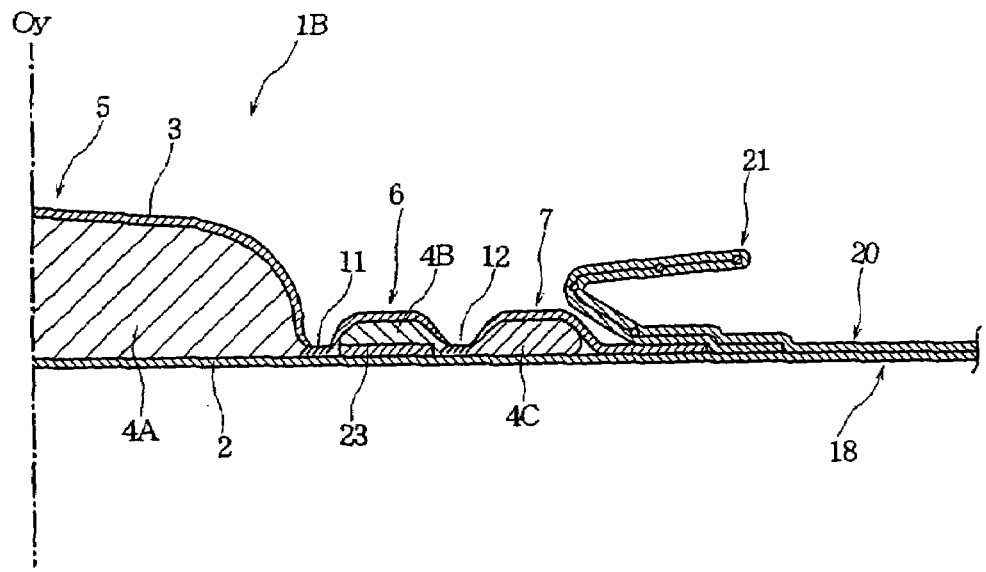
FIG. 7 is a half sectional view showing a sanitary napkin according to a third embodiment of the present invention.

FIG. 7 is a half sectional view showing a sanitary napkin 1B according to a third embodiment of the present invention.

The structure of the sanitary napkin 1B is similar to that of FIG. 1, except that reinforcing members 23 are provided in the resilient portions 6, 6 together with the resilient layers 4B, 4B. The reinforcing members 23 have a higher density and a higher stiffness than the central absorbent layer 4A and the side absorbent layers 4C, and for example, may be a foamed resin material such as foamed urethane resin, an air-laid nonwoven fabric in which pulp and synthetic fibers are thermally fusion-bonded together or fixed together with a binder, or a natural or synthetic rubber in the shape of a rod or plate. With the reinforcing members 23 thus provided, resiliency of the resilient portions 6 can be improved more.

Here, the foamed urethane resin for the reinforcing members 23 may be treated to be hydrophilic and disposed to extend continuously inside the central absorbent portion 5, the first compressed portions 11, the second compressed portions 12 and the resilient portions 6.

In the present invention, it is also possible to eliminate the absorbent layer such as pulp from the resilient portions 6, 6 to leave the reinforcing members 23 alone between the backsheet 2 and the topsheet 3.

Figure 8A:
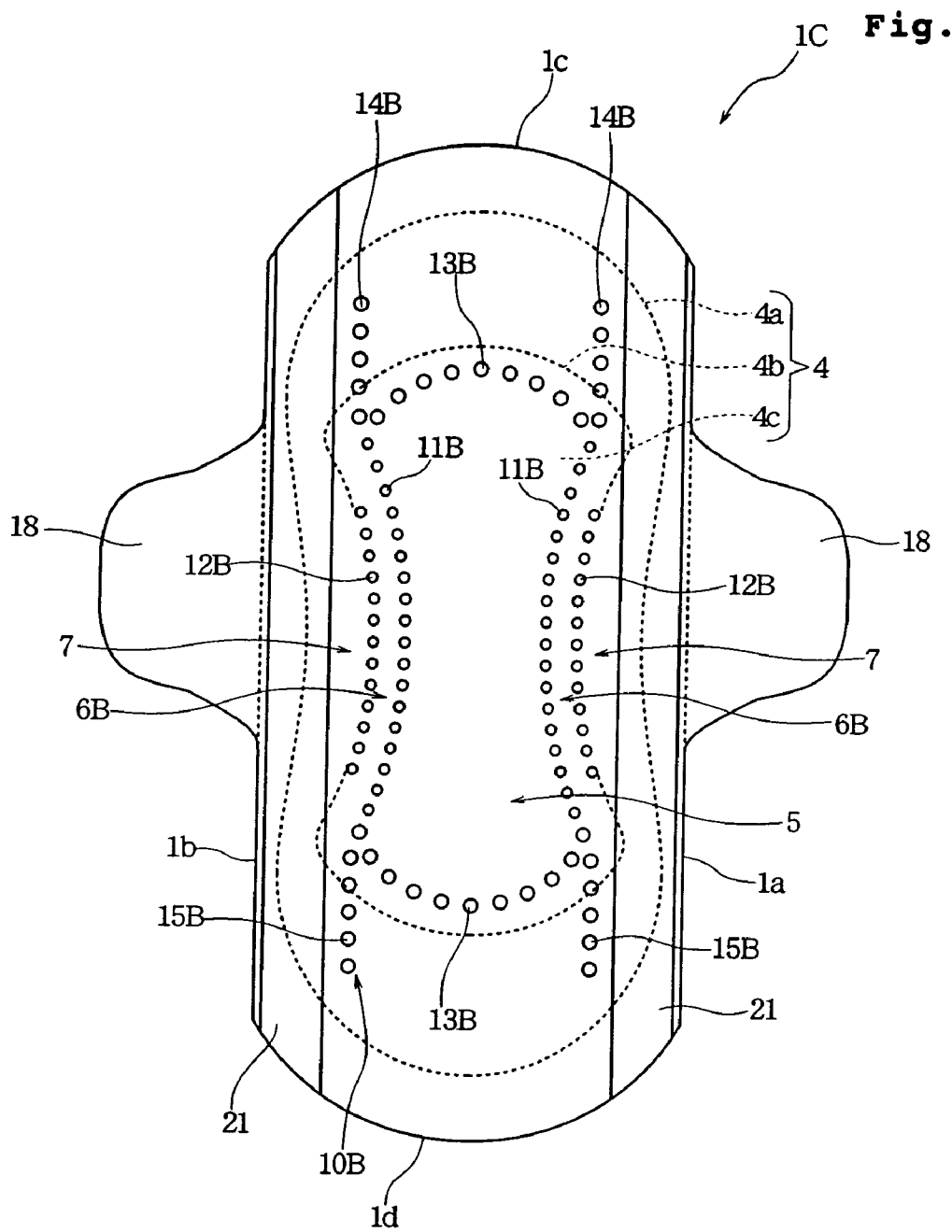
FIG. 8A is a top plan view showing a sanitary napkin according to a fourth embodiment of the present invention.

FIG. 8A is a top plan view showing a sanitary napkin 1C according to a fourth embodiment of the present invention.

In the sanitary napkin 1C, compressed portions 10B are formed in a similar pattern to the compressed potions 10 of FIG. 1. The compressed portions 10B comprise first compressed portion 11B, 11B, second compressed portions 12B, 12B, lateral compressed portions 13B, 13B, forwardly extending compressed portions 14B, 14B and rearwardly extending compressed portions 15B, 15B. However, the compressed portions 10B are not formed as continuously extending compressed grooves but as compressed dots that are arranged at spaced intervals along the pattern.

The compressed portions 10B are formed such that the topsheet 3 and the absorbent layer 4 are heated under pressure only at the dots to have a high density. It should be noted that neither heat nor pressure is applied to locations between adjacent compressed dots when these compressed dots are formed with embossing projections of a dot pattern.

In the sanitary napkin 1C, high-density resilient portions 6B, 6B are formed between the first compressed portions 11B, 11B and the second compressed portions 12B, 12B that are formed as rows of compressed dots. In the resilient portions 6B, 6B, since the restricting force due to the compressed portions 11B and 12B of the compressed dots is weak, there is a limit to compressing the absorbent layer such as pulp to a high density only with the formation of the compressed portions. In this embodiment, therefore, it is desirable to use previously compression-molded pulp or the like for the resilient layers 4B in the resilient portions 6B, 6B. It is also desirable to use the reinforcing members 23, as shown in FIG. 7.

Figure 8B:
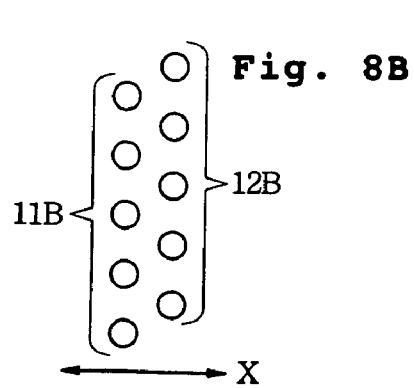
FIGS. 8B and 8C are enlarged top plan views showing the shape of compressed dots.
Figure 8C:
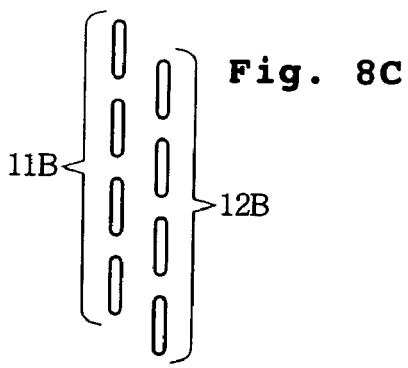

The compressed dots may be in a circular shape, as shown in FIGS. 8A and 8B, or the compressed dots may be in the shape of a longitudinally elongated short line, as shown in FIG. 8C. Preferably, the compressed dots constituting the first compressed portions 11B and the compressed dots constituting the second compressed portions 12B are staggered so that intermediate portions that are left uncompressed and unheated between adjacent compressed dots of the first compressed portions 11B do not overlap laterally (in the X-direction) with intermediate portions that are left uncompressed and unheated between adjacent compressed dots of the second compressed portions 12B, as shown in FIGS. 8B and 8C.

With the compressed dots being thus staggered, when menstrual blood applied to the central absorbent portion 5 is laterally diffused along the topsheet 3 and the absorbent layer, the compressed dots can function as a labyrinth against the lateral migration of the menstrual blood, effectively inhibiting the menstrual blood from migrating to the side portions 7, 7.

Here, one of the first and second compressed portions may be formed as compressed grooves like the compressed portions 10 of FIG. 1, while the other may be formed as rows of compressed dots, as shown in Figs. 8A, 8B and 8C. For example, it is possible that the first compressed portions, the lateral compressed portions, the forwardly extending compressed portions and the rearwardly extending compressed portions are all formed as compressed grooves, while only the second compressed portions are formed as rows of compressed dots. It is also possible that the second compressed portions are formed as compressed grooves, while the first compressed portions are formed as rows of compressed dots wholly or only at regions confronted by the second compressed portions. In these cases, the lateral compressed portions, the forwardly extending compressed portions and the rearwardly extending compressed portions may be formed either as compressed grooves or as rows of compressed dots.

However, it is preferred that the first compressed portions closer to the longitudinal centerline Oy-Oy are formed as compressed grooves while the second compressed portions are formed as rows of compressed dots. In this case, the menstrual blood applied to the central absorbent portion 5 can be certainly inhibited from migrating to the resilient portions 6, 6.

In the case where the compressed portions are formed as rows of compressed dots, as set forth above, since uncompressed portions between adjacent compressed dots can easily be bent in the longitudinal direction, the front and rear portions of the sanitary napkin can easily be bent and deformed to conform to the abdomen and buttocks, respectively. Particularly when the compressed dots are staggered, as shown in FIGS. 8B and 8C, the effect of bending can be enhanced without increasing the bending stiffness of the compressed portions.

In the case where short line-shaped compressed dots are formed, as shown in FIG. 8C, it is preferred that the short line-shaped compressed dots have a length of about 10 to 20 mm and intermediate portions (uncompressed portions) between short line-shaped compressed dots adjacent each other in the longitudinal direction have a length of about 5 to 10 mm. Here, the individual short line-shaped compressed dots may be formed by alternating the high-density compressed portions 10a with the medium-density compressed portions 10b. The compressed portions shown in FIG. 1 may be interrupted at an arbitrary position.

Referring to FIG. 9 through FIG. 13, yet other embodiments will be described hereinbelow. The compressed portions in the first through fourth embodiments are formed in the same or similar pattern, but compressed portions in the embodiments shown in FIG. 9 through FIG. 13 are formed in patterns different from that of the first through fourth embodiments.

Regarding the constructions but for the patterns of the compressed portions, however, the constructions shown in the first through fourth embodiments may, of course, be selectively adopted for the embodiments shown in FIG. 9 through FIG. 13. Hereinbelow, therefore, described will be only the difference in pattern of the compressed portions, while the detailed description of the other portions will be omitted by designating them by the reference numerals common to the individual embodiments.

Figure 9:
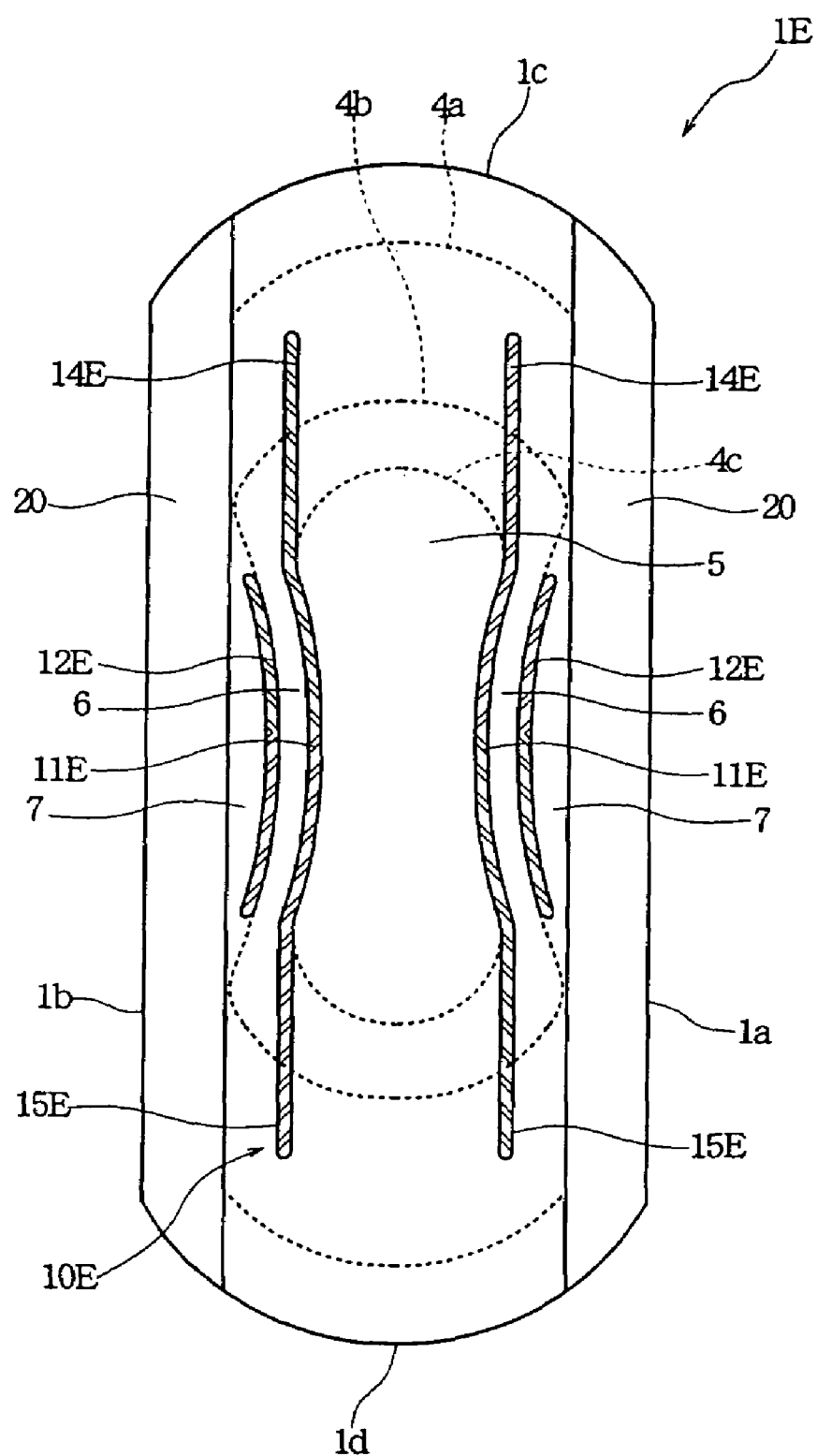
FIG. 9 is a top plan view showing a sanitary napkin according to a fifth embodiment of the present invention.

FIG. 9 is a top plan view showing a sanitary napkin 1E according to a fifth embodiment of the present invention.

Compressed portions 10E provided in the sanitary napkin 1E of FIG. 9 do not include the lateral compressed portions 13, 13 of FIG. 1, so that forwardly extending compressed portions 14E, 14E and rearwardly extending compressed portions 15E, 15E are continuously extended forwardly and rearwardly from first compressed portions 11E, 11E in the shape of an arcuate line. The region between the first compressed portions 11E, 11E is the central absorbent portion 5. Second compressed portions 12E, 12E are disposed outside the central absorbent portion 5.

The second compressed portions 12E, 12E are also formed in the shape of an arcuate line and spaced a constant distance apart from the first compressed portions 11E, 11E.

Also in this embodiment, the resilient portions 6, 6 can exhibit sufficient resiliency in the deformed state of FIGS. 4 and 5. In addition, since menstrual blood applied to the absorbent layer can diffuse from the central absorbent portion 5 between the first compressed portions 11E, 11E into the portion between the forwardly extending compressed portions 14E, 14E and the portion between the rearwardly extending compressed portions 15E, 15E, the length of the sanitary napkin 1E can be fully exploited when a large amount of menstrual blood is applied.

FIG. 10 is a top plan view showing a sanitary napkin 1F according to a sixth embodiment of the present invention.

The sanitary napkin 1F is elongated and its width between the right side edge 1a and the left side edge 1b is increased at its rear portion to provide what is called hip-guard.

In this embodiment, first rear compressed portions 15F, 15F are extended rearwardly from first compressed portions 11F, 11F in such a manner that they gradually approach each other toward the rear end edge 1d and are connected to each other inside the rear end edge 1d through a connecting compressed portion 17F in the shape of a curved line.

Outside the first rear compressed portions 15F, 15F, moreover, second rear compressed portions 18F, 18F are provided and connected to each other inside the rear end edge 1d through a connecting compressed portion 19F in the shape of a curved line. The second rear compressed portions 18F, 18F are also provided with portions that gradually approach each other toward the rear end edge 1d.

In this embodiment, the region surrounded by the first compressed portions 11F, 11F and lateral compressed portion 13F is a central absorbent portion 5F, while the region surrounded by the first rear compressed portions 15F, 15F and the connecting compressed portion 17F is a rear central absorbent portion 5G. The bulky central absorbent layer 4A continuously extends over the central absorbent portion 5F and the rear central absorbent portion 5G, between the topsheet 3 and the backsheet 2. In the central absorbent portion 5F and the rear central absorbent portion 5G, the density and basis weight of the central absorbent layer 4A are almost uniform.

Between the first rear compressed portions 15F, 15F and the second rear compressed portions 18F, 18F, moreover, there are provided rear resilient portions 6F, 6F, in which the absorbent layer (resilient layer) between the topsheet 3 and the backsheet 2 has a higher density than the central absorbent layer 4A in the rear central absorbent portion 5G. The density of the absorbent layer in the rear resilient portions 6F, 6F is equal to or slightly lower than that in the resilient portions 6, 6 and higher than that of the central absorbent layer 4A.

As shown in FIG. 10, boundary portions between the first rear compressed portions 15F, 15F and the first compressed portions 11F, 11F are curved away from the longitudinal centerline Oy-Oy, so that the central absorbent layer 4A is widened at these boundary portions. The first rear compressed portions 15F, 15F gradually approach each other as they extend from the boundary portions toward the rear end edge 1d, while the first compressed portions 11F, 11F also gradually approach each other as they extend from the boundary portions to the lateral reference line Ox-Ox.

On right and left sides of the skin surface of the sanitary napkin 1F, the liquid-impermeable sheets 20, 20 and the leakage preventing walls 21, 21 formed of the liquid-impermeable sheets 20, 20 are provided. The leakage preventing walls 21, 21 are of the same construction as those shown in FIG. 1 except for dimensions. The boundary line between the bonded region and the unbonded region in the first panel 21a includes the intermediate boundary line 22a, the front boundary line 22b and the rear boundary line 22c, wherein 24a indicates the front rising point of the leakage preventing wall 21, while 24b indicates the rear rising point of the leakage preventing wall 21.

Also in this embodiment, the front rising point 24a is in proximity to the front end of the resilient portion 6, and the least straight-line distance between the rising point 24a and the front end 12a of the second compressed portion 12F is 45 mm or less, preferably 40 mm or less, more preferably 25 mm or less.

Likewise, the rear rising point 24b is in proximity to the front end of the rear resilient portion 6F, and the distance between the rising point 24b and a front end 18G of the second rear compressed portion 18F is 45 mm or less. In case of the sanitary napkin 1F of FIG. 10 that is long and suitable for night-time use with the first rear compressed portions 15F, the second rear compressed portions 18F and the hip-guard, however, the hip-guard intended to contact the buttocks is easily twisted or distorted. Accordingly, the least straight-line distance between the rear rising point 24b of the leakage preventing wall 21 and the front end 18G of the second rear compressed portion 18F is preferably 20 mm or less.

When the long sanitary napkin 1F is worn as attached to the inner side of the groin piece 25 of the undergarment, the lateral reference line Ox-Ox can match the longitudinal nearly center of the vaginal opening.

When the compressive force F is applied to the vicinity of the lateral reference line Ox-Ox from the thighs, therefore, the sanitary napkin 1F at this portion can be deformed as shown in FIGS. 4 and 5, and then, when the compressive force F is relieved, the sanitary napkin 1F can be restored from the deformed state of FIGS. 4 and 5 to its original state due to the resiliency of the resilient portions 6, 6.

Here, the rear portion of the sanitary napkin 1F is brought into contact with the buttocks so that the rear central absorbent portion 5G may fit in the cleft of the buttocks. Since the rear resilient portions 6F, 6F are provided on both sides of the rear central absorbent portion 5G, the rear portion is hardly deformed even if the sanitary napkin 1F is subjected to an excessive pressure from the wearer's body or undergarment caused by change of wearer's position (posture) or can be easily restored after deformation, so that the rear central absorbent portion 5G can be certainly kept in close contact with the wearer's body.

Moreover, since the front rising point 24a of the leakage preventing wall 21 is in proximity to the resilient portion 6 and the rear rising point 24b is in proximity to the rear resilient portion 6F, the positions of the rising points 24a and 24b can be stabilized during wear, thereby preventing the leakage preventing wall 21 from twisting or falling down on the central absorbent portion 5F and the rear central absorbent portion 5G.

In case where the sanitary napkin 1F is worn together with a sanitary panty in which an elastic member is provided from a groin piece to a back body to extend along the cleft of the wearer's buttocks, the rear central absorbent portion 5G is pushed into the cleft of the buttocks due to a force of the elastic member. At this time, since the first rear compressed portions 15F, 15F and the second rear compressed portions 18F, 18F are provided on two sides of the rear central absorbent portion 5G and can individually serve as a flexible hinge, the rear central absorbent portion 5G subjected to the pushing force from the undergarment can be easily brought into close contact with the buttocks.

Figure 11:
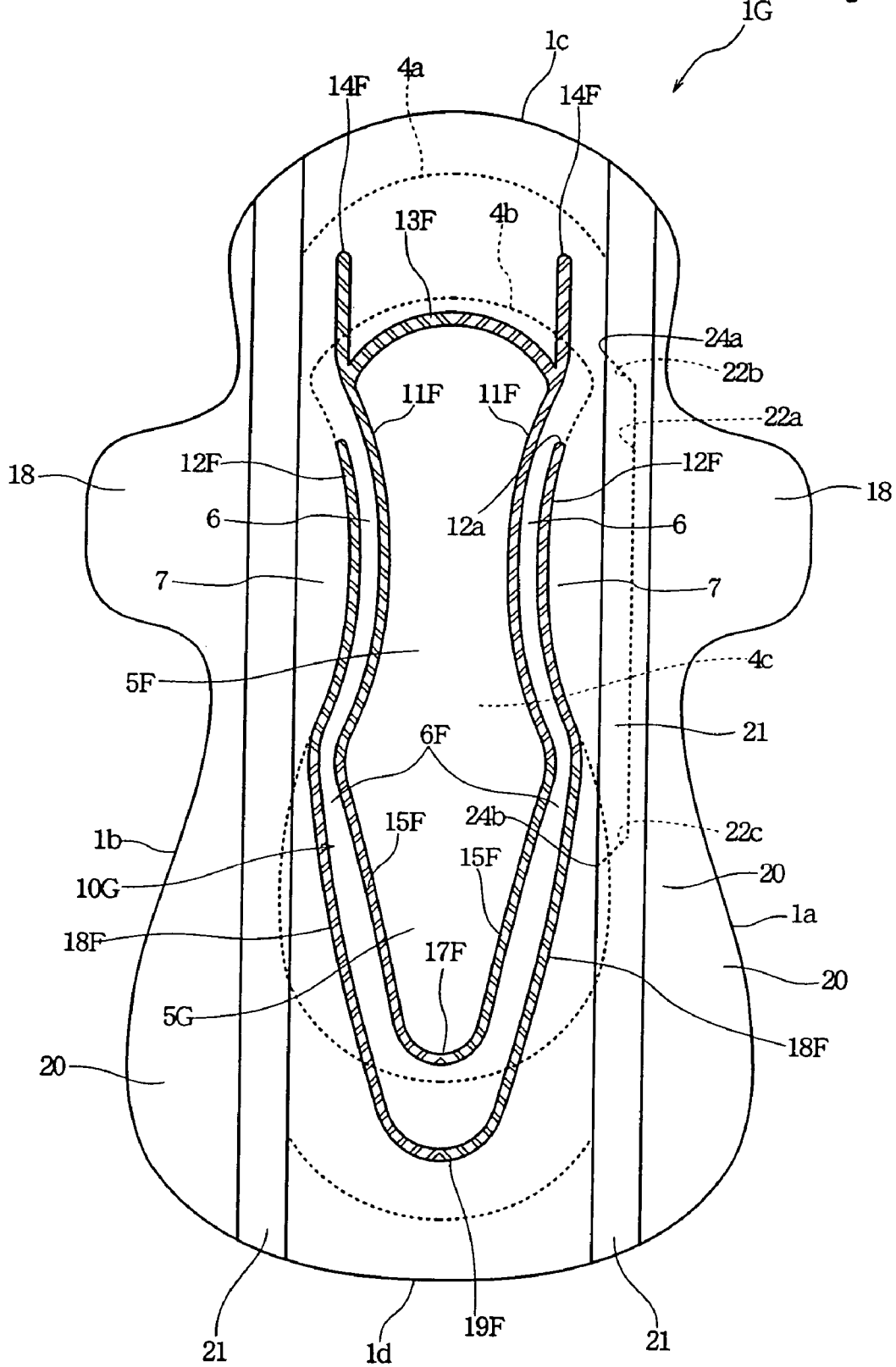
FIG. 11 is a top plan view showing a sanitary napkin according to a seventh embodiment of the present invention.

FIG. 11 is a top plan view showing a sanitary napkin 1G according to a seventh embodiment of the present invention.

Although a hip-guard is provided at its rear portion, the sanitary napkin 1G of FIG. 11 is of a slightly shorter longitudinal dimension than the sanitary napkin 1F of FIG. 10.

The sanitary napkin 1G has compressed portions 10G that are formed in the substantially same pattern as the compressed potions 10F of FIG. 10, except that the second compressed portions 12F, 12F are continued to the second rear compressed portions 18F, 18F. Also in this sanitary napkin 1G, since the resilient portions 6, 6 are provided on two sides of the central absorbent portion 5F, sufficient resilience can be produced against an external deforming force.

Here, the straight-line distance between the front rising point 24a of the leakage preventing wall 21 and the front end 12a of the second compressed portion 12F is 45 mm or less, preferably 40 mm or less, more preferably 25 mm or less. The least straight-line distance between the rear rising point 24b and the second compressed portion 18F is also 45 mm or less, preferably 25 mm or less. In the embodiment of FIG. 11 where the rising point 24b is located between the second rear compressed portion 18F and the right side edge 1a, however, the straight-line distance may be considerably decreased, for example, to 15 mm or less.

Accordingly, the individual rising points 24a and 24b, particularly the rear rising point 24b, can be certainly reinforced by the rear resilient portion 6F, thereby preventing the leakage preventing wall 21 from twisting or falling down.

Figure 12:
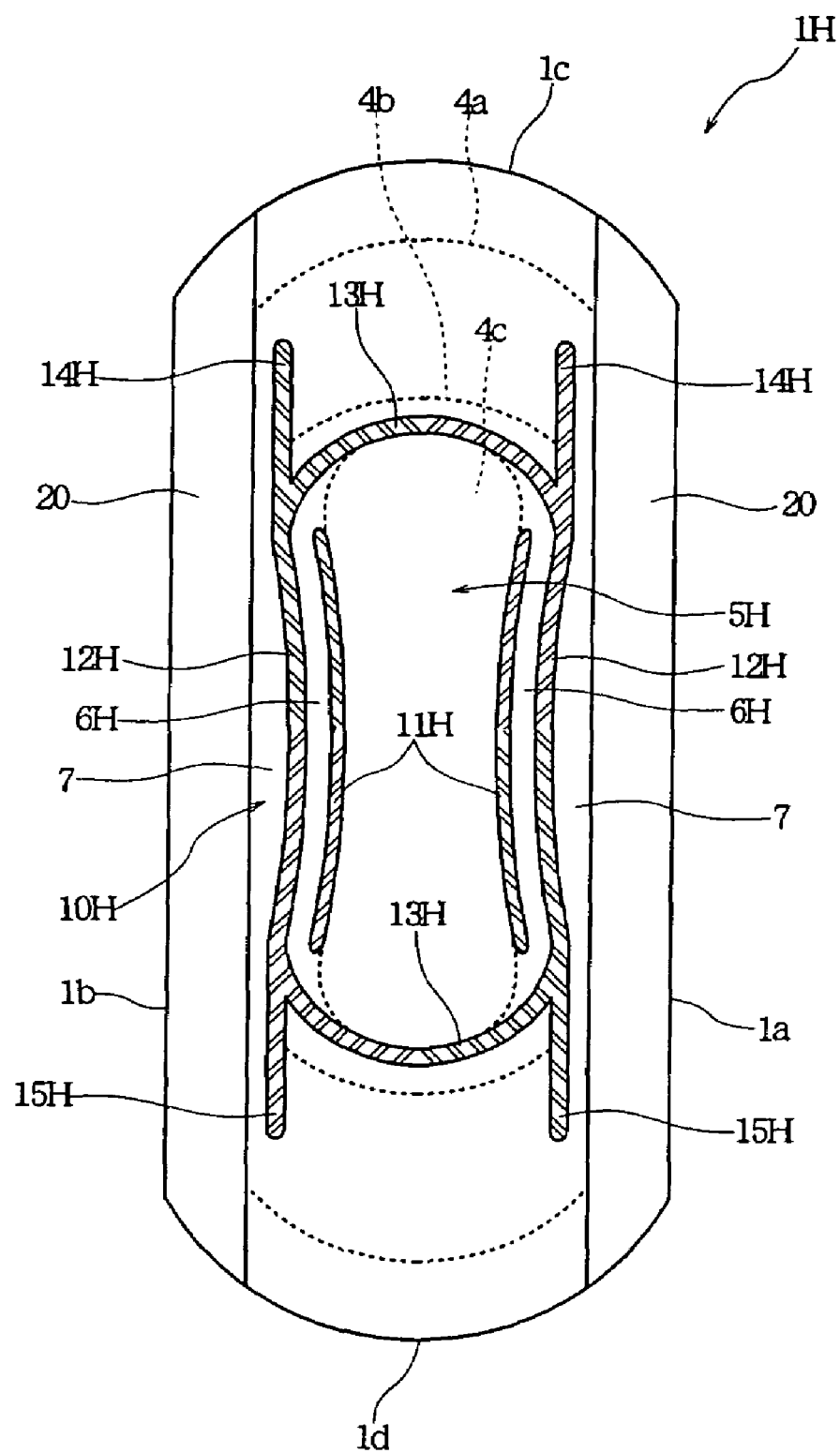
FIG. 12 is a top plan view showing a sanitary napkin according to an eighth embodiment of the present invention.

FIG. 12 is a top plan view showing a sanitary napkin 1H according to an eighth embodiment of the present invention.

The structure of the sanitary napkin 1H is similar to that of the sanitary napkin 1 shown in FIG. 1, except that the wings 18 are eliminated.

The sanitary napkin 1H of FIG. 12 has compressed portions 10H comprising first compressed portion 11H, 11H that extend in the shape of an arcuate line and second compressed portions 12H, 12H that also extend in the shape of an arcuate line outside the former, wherein the first compressed portion 11H, 1H are spaced a constant distance apart from the second compressed portions 12H, 12H. The region between the first compressed portion 11H, 11H is a central absorbent portion 5H, while the regions between the first compressed portion 11H, 11H and the second compressed portions 12H, 12H are resilient portions 6H, 6H.

The second compressed portions 12H, 12H are connected to each other through lateral compressed portions 13H, 13H provided at front and rear portions. Therefore, the first compressed portion 11H, 11H and the resilient portions 6H, 6H are located inside the region surrounded by the second compressed portions 12H, 12H and the lateral compressed portions 13H, 13H.

Furthermore, forwardly extending compressed portions 14H, 14H and rearwardly extending compressed portions 15H, 15H are formed to extend continuously from the second compressed portions 12H, 12H.

Also in the sanitary napkin 1H, the resilient portions 6H, 6H can produce sufficient lateral resilience.

In this embodiment, since the region surrounded by the second compressed portions 12H, 12H and the lateral compressed portions 13H, 13H has a larger area than the central absorbent portion 5H, liquid absorption capacity of the surrounded region can be made large. In addition, since diffusion of menstrual blood applied to the resilient portions 6H, 6H between the first compressed portion 11H, 11H and the second compressed portions 12H, 12H can be limited in the surrounded region, leakage of menstrual blood from the sanitary napkin 1H can be prevented easily.

Figure 13:
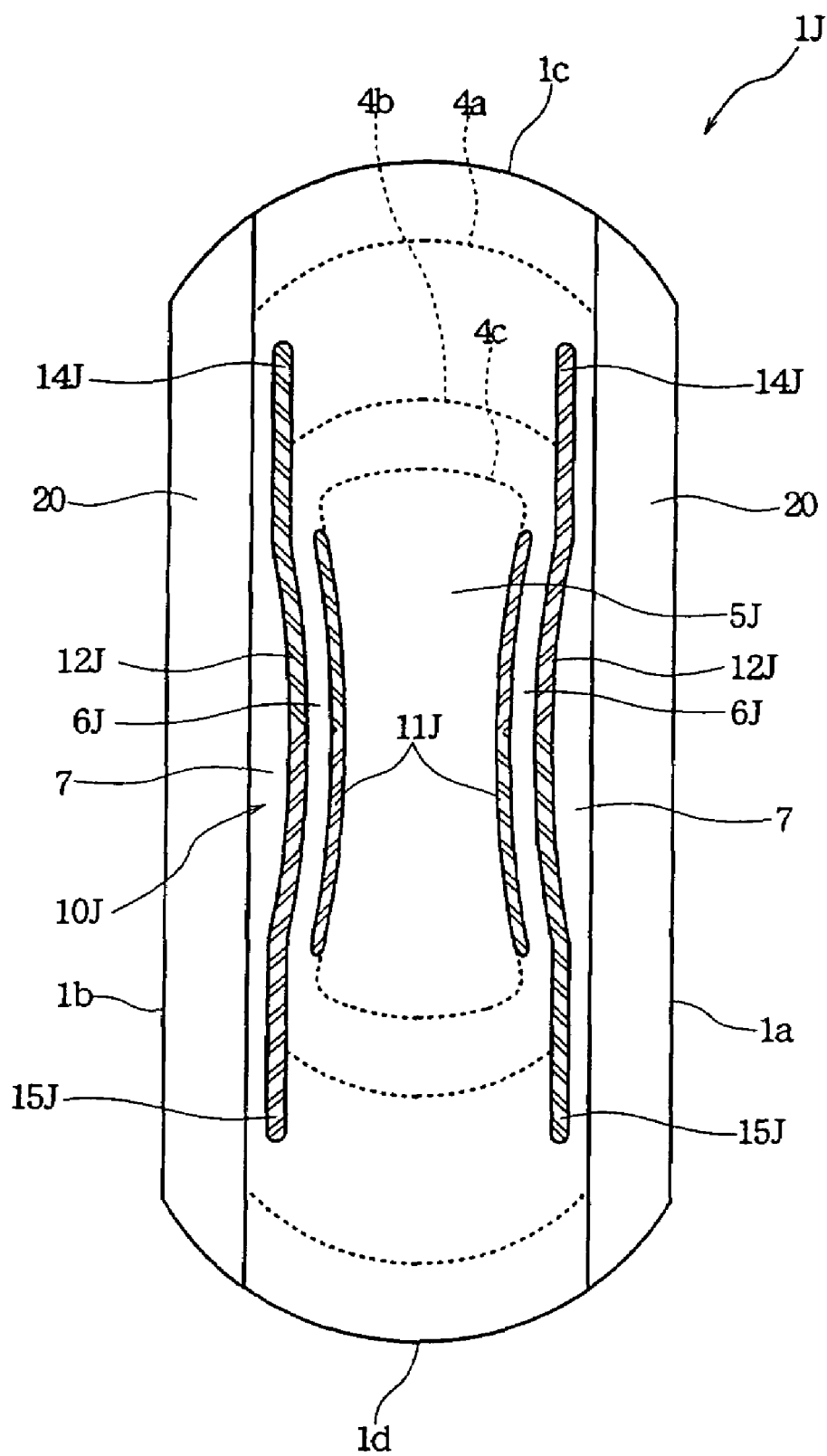
FIG. 13 is a top plan view showing a sanitary napkin according to a ninth embodiment of the present invention.

FIG. 13 is a top plan view showing a sanitary napkin 1J according to a ninth embodiment of the present invention.

The sanitary napkin 1J has compressed portions 10J whose pattern is slightly changed from that in the sanitary napkin 1E of FIG. 9. In this embodiment, forwardly extending compressed portions 14J, 14J and rearwardly extending compressed portions 15J, 15J are continuously extended forwardly and rearwardly from second compressed portions 12J, 12J. On the other hand, first compressed portions 11J, 11J are provided in the region between the second compressed portions 12J, 12J. The region between the first compressed portions 11J, 11J is a central absorbent portion 5J.

Also in this embodiment, sufficient lateral resilience against compression can be produced by the action of resilient portions 6J, 6J. In addition, since region outside the central absorbent portion 5J is positioned between the second compressed portions 12J, 12J, the forwardly extending compressed portions 14J, 14J and the rearwardly extending compressed portions 15J, 15J over a long range in the longitudinal direction, menstrual blood adhered to the resilient portions 6J, 6J can be diffused in the longitudinal direction of the sanitary napkin 1J, thereby improving the effect of preventing lateral leakage.

Next, a method for manufacturing the sanitary napkin will be described.

Hereinafter a method for manufacturing the sanitary napkin 1 shown in FIG. 1 and FIGS. 2A and 2B will be described, but the sanitary napkins according to the other embodiments can be manufactured in a similar manner by changing the pattern of the compressed portions or changing the materials to be disposed between the first compressed portion 11 and the second compressed portion 12.

In the manufacturing method of the sanitary napkin 1, at first, the absorbent layer 4 and the topsheet 3 are stacked one upon another and optionally bonded to each other. Then, the stack is pressed with the pressure member having an embossed pattern from the side of the topsheet 3, to thereby form the compressed portions 10. Subsequently, the backsheet 2 is laid on and bonded to the stack. Here, it is possible to emboss only the absorbent layer 4 and then hold it between the backsheet 2 and the topsheet 3. The embossing may be performed from the side of the exterior surface (garment surface) of the absorbent layer 4 or from both sides. In the followings, however, the case where the stack of the absorbent layer 4 and the topsheet 3 is embossed from the side of the topsheet 3 will be described.

Figure 14A:
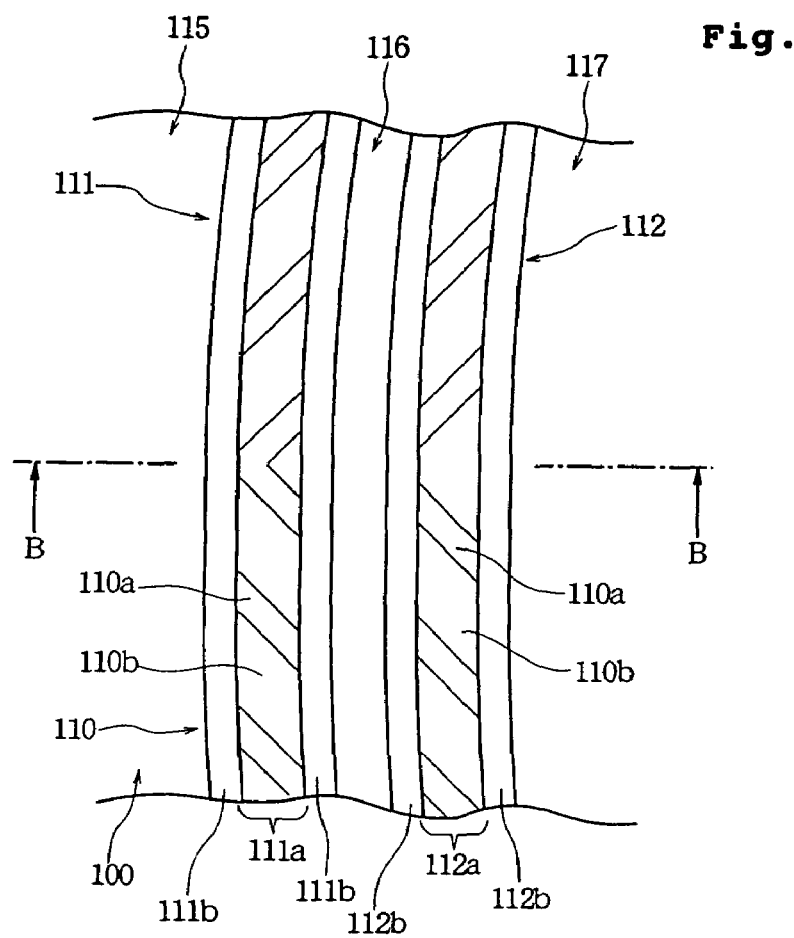
Figure 14B:
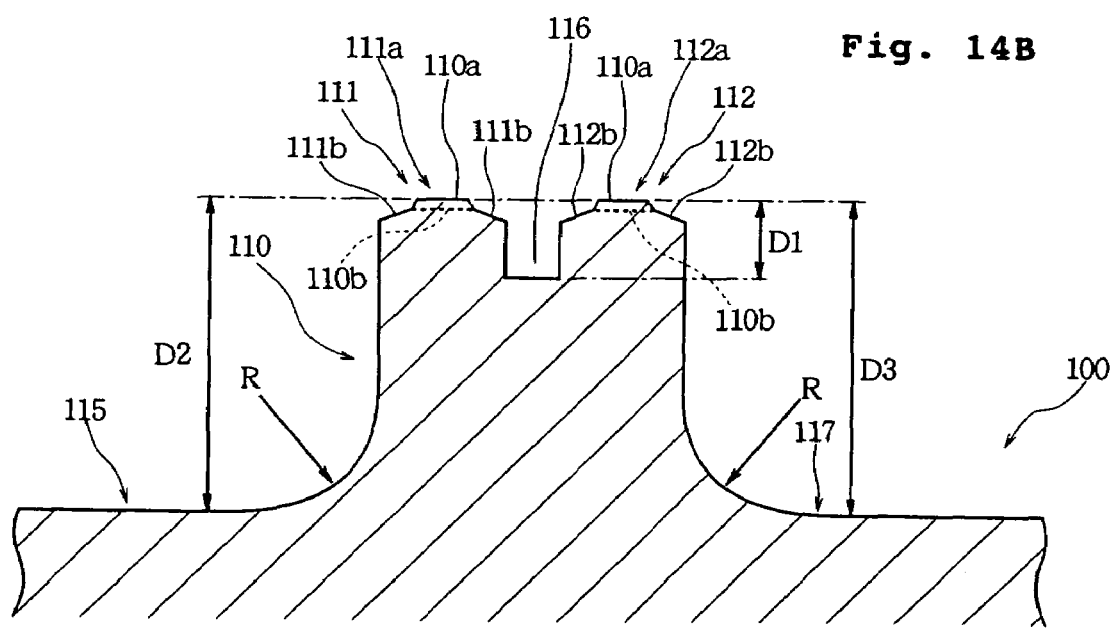
Figure 15:
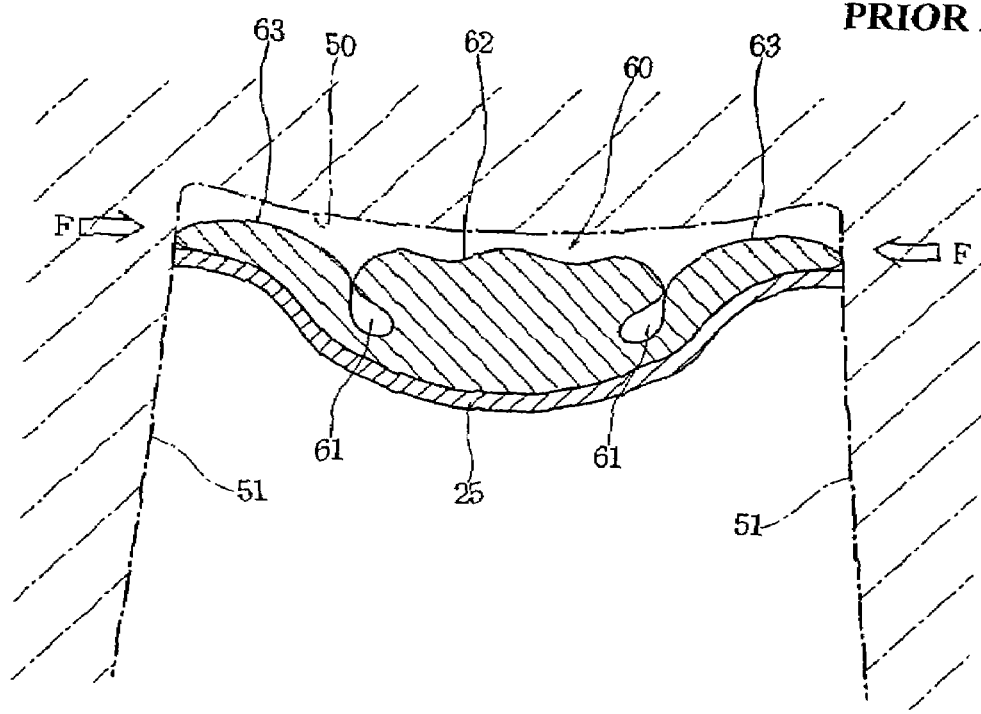
FIG. 15 is sectional view illustrating problems of a conventional sanitary napkin worn in the wearer's crotch.

FIG. 14A is a plan view showing a portion of a pressure member 100 from the side of a pressing surface thereof, and FIG. 14B is a sectional view taken along lone B-B of FIG. 14A.

The pressure member 100 has an embossing projection 110 whose pattern can be transferred to the stack as the compressed portions 10 shown in FIG. 1. In FIG. 14A, illustrated is only a portion of the embossing projection 110 that forms the first and second compressed portions 11 and 12 in the vicinity of the lateral reference line Ox-Ox of FIG. 1.

In FIGS. 14A and 14B, a first base 115 for facing the central absorbent portion 5 of the sanitary napkin 1 is provided on the left side of the embossing projection 110, while a second base 117 for facing the side portion 7 is provided on the right side. Here, the depth from the top of the embossing projection 110 to the first base 115 is indicated by D2, while the depth form the top to the second base 117 is indicated by D3. The depths D2 and D3 may be equal or the first base 115 may be made deeper because it is intended to face the central absorbent portion 5 that is relatively thick.

FIGS. 14A and 14B show a first projection 111 for forming the first compressed portion 11 and a second projection 112 for forming the second compressed portion 12. Between the first projection 111 and the second projection 112, as shown in FIG. 14B, there is formed a recess 116 for compressing the absorbent layer at a location between the first compressed portion 11 and the second compressed portion 12. In this embodiment, the resilient portion 6 is formed by the recess 116. The depth D1 from the top to the bottom of the recess 116 is sufficiently smaller than the depths D2 and D3.

The first projection 111 has a pressing portion 111a at the tip thereof, and inclined surfaces 111b, 111b that are inclined away from the top are formed at both sides thereof Likewise, the second projection 112 has a pressing portion 112a at the tip thereof, and inclined surfaces 112b, 112b are formed in the same manner. Here, the inclined surfaces 111b and 112b may be steep slopes continuing to the bottom of the recess 116.

Along the pressing portions 111a and 112a, pressing surfaces 110a for forming the high-density compressed portions 10a alternate with shallow grooves 110b for forming the medium-density compressed portions 10b. The pressing surfaces 110a and the shallow grooves 110b are formed in the same pattern as the high-density compressed portions 10a and the medium-density compressed portions 10b.

On the other hand, projections for forming portions of the first compressed portions 11 that are not confronted by the second compressed portions 12 in FIG. 1, projections for forming the lateral compressed portions 13, projections for forming the forwardly extending compressed portions 14 and projections for forming the rearwardly extending compressed portions 15 are formed such that only the first projection 111 rises from the first and second bases 115 and 117, without having the second projection 112 alongside of the first projection 111 as in FIGS. 14A and 14B.

After stacking the absorbent layer 4 and the topsheet 3 one upon another and optionally bonding them to each other, the pressure member 100 of FIGS. 14A and 14B is applied to the surface of the topsheet 3 while another pressure member having a smooth surface is applied to the exterior surface of the absorbent layer 4, so that the absorbent layer 4 and the topsheet 3 are pressed with the two pressure members. Here, the pressure members may be heated for pressing, if necessary. As a result, the compressed portions 10 are formed in the stack, as shown in FIG. 1.

At this time, since the absorbent layer 4 is pressed with the recess 116 of the depth D1, the absorbent layer is highly compressed at a location between the first compressed portion 11 and the second compressed portion 12. Here, the highly compressed absorbent layer is restricted by the topsheet 3 between the first compressed portion 11 and the second compressed portion 12.

On the other hand, the central absorbent portion 5 is not substantially pressed or hardly pressed with the first base 115. Likewise, the side portion 7 is not substantially pressed or hardly pressed with the second base 117. Thus, the absorbent layer can be highly compressed at a location between the first compressed portion 11 and the second compressed portion 12 to have a density sufficiently higher than those in the central absorbent portion 5 and the side portions 7.

In the foregoing embodiments, the highly compressed absorbent layer is the resilient layer 4B. The highly compressed absorbent layer formed between the compressed portions 11 and 12 can serve not only as the resilient layer 4B but also as a support member for supporting the central absorbent portion 5 from below and bringing it into close contact with the vaginal opening when the sanitary napkin 1 is in the deformed state of FIG. 4.

It should be noted that the pressure member 100 and the pressure member having a smooth surface may be constructed as surface structures of rolls facing each other or as flat pressure members. With the recess 116 thus provided, the absorbent layer may be highly compressed at a location between the first compressed portion 11B and the second compressed portion 12B that are formed of compressed dots, as shown in FIG. 8.

According to the present invention, as has been described hereinabove, the ability to laterally restore the central absorbent portion when a lateral compressive force applied thereto is relieved, can be improved. In addition, the absorbent article can be easily restored from other deformations such as twisting. Accordingly, it can be kept in close contact with the excretory part of the wearer's body at all times, thereby preventing lateral leakage of discharged liquid.

Although the present invention has been illustrated and described with respect to exemplary embodiments thereof, it should be understood by those skilled in the art that the foregoing and various other changes, omission and additions may be made therein and thereto, without departing from the spirit and scope of the present invention. Therefore, the present invention should not be understood as limited to the specific embodiments set out above but to include all possible embodiments which can be embodied within a scope encompassed and equivalent thereof with respect to the feature set out in the appended claims.

What is claimed is:

1. An absorbent article comprising:
   a liquid-permeable topsheet on a skin surface;
   a backsheet on a garment surface;
   an absorbent layer between the topsheet and the backsheet;
   first compressed portions and second compressed portions, in which the absorbent layer is compressed together with at least the topsheet, extend longitudinally of the absorbent article, the first compressed portions being disposed symmetrically about a longitudinal centerline of the absorbent article to define a central absorbent portion having a first portion of the absorbent layer therebetween, the second compressed portions being disposed symmetrically about the longitudinal centerline and spaced outwardly apart from the first compressed portions; and
   resilient portions defined between each adjacent pair of first and second compressed portions and including a second portion of the absorbent layer between said first and second compressed portions having a higher density than the first portion of the absorbent layer in the central absorbent portion;
   wherein:
   the first compressed portions are inwardly curved toward the longitudinal centerline within a region disposed about a lateral centerline of the absorbent article, said region extending along less than an entire length of the absorbent article along the longitudinal centerline,
   the second compressed portions are each shorter than corresponding first compressed portions and extend only within said region disposed about the lateral centerline,
   each of the first compressed portions and the second compressed portions comprising compressed grooves most substantially recessed toward the backsheet, and
   when the central absorbent portion is laterally compressed by an external force, the resilient portions defined between each adjacent pair of first and second compressed portions are permitted to exert a resilience against compression on the central absorbent portion.

2. An absorbent article as set forth in claim 1, wherein in the individual resilient portions, the absorbent layer is compressed due to formation of the first and second compressed portions.

3. An absorbent article as set forth in claim 1, wherein in the individual resilient portions, the absorbent layer of hydrophilic fibers is compressed together with a nonwoven fabric of synthetic fibers due to formation of the first and second compressed portions.

4. An absorbent article as set forth in claim 3, wherein also in the individual first compressed portions, the absorbent layer is compressed together with the nonwoven fabric.

5. An absorbent article as set forth in claim 3, wherein the nonwoven fabric is a through-air bonded nonwoven fabric.

6. An absorbent article as set forth in claim 1, wherein between the topsheet and the backsheet, the individual resilient portions have a resilient reinforcing member alone or in combination with the absorbent layer that is compressed due to formation of the first and second compressed portions.

7. An absorbent article as set forth in claim 1, wherein the resilient portions approach each other the nearest at a lateral reference line of the absorbent article, and extend gradually away from the centerline as they extend away from the lateral reference line toward longitudinally opposed ends of the absorbent article.

8. An absorbent article as set forth in claim 1, wherein the individual resilient portions are in the shape of a line curved toward the centerline.

9. An absorbent article as set forth in claim 1, wherein the individual resilient portions have a portion of constant width, over which the first and second compressed portions are spaced a constant distance apart from each other.

10. An absorbent article as set forth in claim 1, wherein side portions are each defined between each second compressed portion and a corresponding longitudinally extending side edge of the absorbent article, and an elastic shrinkage force is longitudinally exerted on the side portions.

11. An absorbent article as set forth in claim 10, wherein longitudinally extending sheets are disposed on the skin surface with the central absorbent portion externally exposed therebetween, the individual sheets being fixed on the skin surface at front and rear portions thereof while being raised from the skin surface at an intermediate portion thereof to form a leakage preventing wall, wherein at least one of front and rear rising points of the leakage preventing wall is in proximity to the second compressed portion.

12. An absorbent article as set forth in claim 11, wherein the rising points are in proximity to ends of the second compressed portion.

13. An absorbent article as set forth in claim 11, wherein the proximity means that a distance is 45 mm or less.

14. An absorbent article as set forth in claim 10, wherein first rear compressed portions are disposed to gradually approach each other as they extend continuously from the first compressed portions toward a rear edge of the absorbent article, and second rear compressed portions are each disposed between each first rear compressed portion and corresponding one of the side edges and spaced apart from the first rear compressed portions, wherein
   longitudinally extending sheets are disposed on the skin surface with the central absorbent portions externally exposed therebetween, the individual sheets being fixed on the skin surface at front and rear portions thereof while being raised from the skin surface at front and rear portions thereof while being raised from the skin surface at an intermediate portion thereof to form a leakage preventing wall, wherein
   a front rising point of the leakage preventing wall is in proximity to the first compressed portions while a rear rising point of the leakage preventing wall is in proximity to the second rear compressed portion.

15. An absorbent article as set forth in claim 14, wherein the rear rising point of the leakage preventing wall is in proximity to a front end of the second rear compressed portion.

16. An absorbent article as set forth in claim 10, wherein the second portion of the absorbent layer in each individual resilient portion located between said first and second compressed portions has a higher basis weight than a third portion of the absorbent layer in a corresponding side portion defined between a corresponding second compressed portion and a corresponding longitudinally extending side edge of the absorbent article.

17. An absorbent article as set forth in claim 10, wherein the second portion of the absorbent layer in each individual resilient portion comprises two absorbent layers, and
   a third portion of the absorbent layer in a corresponding side portion defined between a corresponding second compressed portion and a corresponding longitudinally extending side edge of the absorbent article comprises only a single absorbent layer.

18. An absorbent article as set forth in claim 1, which is a sanitary napkin.

19. An absorbent article as set forth in claim 1, wherein the second portion of the absorbent layer in each individual resilient portion located between said first and second compressed portions is compressed to have a higher density than the first portion of the absorbent layer in the central absorbent portion.

20. An absorbent article as set forth in claim 1, wherein the second portion of the absorbent layer in each individual resilient portion located between said first and second compressed portions has a higher basis weight than the first portion of the absorbent layer in the central absorbent portion.

* * * * *